United States Patent
Jiang et al.

(10) Patent No.: US 10,468,203 B2
(45) Date of Patent: Nov. 5, 2019

(54) EDIBLE SUPERCAPACITORS

(71) Applicant: ARIZONA BOARD OF REGENTS ON BEHALF OF ARIZONA STATE UNIVERSITY, Scottsdale, AZ (US)

(72) Inventors: Hanqing Jiang, Chandler, AZ (US); Prithwish Chatterjee, Tempe, AZ (US); Wenwen Xu, Mesa, AZ (US); Xu Wang, Tempe, AZ (US)

(73) Assignee: Arizona Board of Regents on Behalf of Arizona State University, Scottsdale, AZ (US)

( * ) Notice: Subject to any disclaimer, the term of this patent is extended or adjusted under 35 U.S.C. 154(b) by 66 days.

(21) Appl. No.: 15/755,027

(22) PCT Filed: Aug. 25, 2016

(86) PCT No.: PCT/US2016/048602
§ 371 (c)(1),
(2) Date: Feb. 23, 2018

(87) PCT Pub. No.: WO2017/035318
PCT Pub. Date: Mar. 2, 2017

(65) Prior Publication Data
US 2018/0235881 A1    Aug. 23, 2018

Related U.S. Application Data

(60) Provisional application No. 62/292,625, filed on Feb. 8, 2016, provisional application No. 62/209,695, filed on Aug. 25, 2015.

(51) Int. Cl.
*H01G 11/68* (2013.01)
*H01G 11/30* (2013.01)
(Continued)

(52) U.S. Cl.
CPC .............. *H01G 11/68* (2013.01); *A23L 33/16* (2016.08); *A61N 1/32* (2013.01); *H01G 11/30* (2013.01);
(Continued)

(58) Field of Classification Search
CPC ........ H01G 11/30; H01G 11/52; H01G 11/54; H01G 11/68; H01G 11/78
See application file for complete search history.

(56) References Cited

U.S. PATENT DOCUMENTS 6,998,190 B2 * 2/2006 Nobuta .................... H01G 9/10
429/149
8,405,955 B2 * 3/2013 Gadkaree ............... H01G 11/38
361/502
(Continued)

FOREIGN PATENT DOCUMENTS

| CN | 1434531 A | 8/2003 |
| CN | 1938802 A | 3/2007 |

(Continued)

OTHER PUBLICATIONS

Agostoni, E. Riva, M. Giovannini, Dietary fiber in weaning foods of young children. Pediatrics 96, 1002-1005 (1995).
(Continued)

*Primary Examiner* — Eric W Thomas
(74) *Attorney, Agent, or Firm* — Michael Best & Friedrich LLP

(57) ABSTRACT

Systems and methods are described for an edible capacitive power source such as a supercapacitor device. The capacitive power source includes an anode electrode, an anode current collector, a cathode electrode, and a cathode current collector, arranged in layers with a separator layer positioned between the anode electrode and the cathode electrode forming a symmetrical electrical double-layer capaci-
(Continued)

tor. The anode electrode, the anode current collector, the cathode electrode, the cathode current collector, and the separator layer are all constructed of non-toxic, edible materials. The packaging material, the conductive anode tab, and the conductive cathode tab are all also constructed of non-toxic, edible materials forming a completely edible capacitive power source package.

19 Claims, 16 Drawing Sheets

(51) Int. Cl.
    *H01G 11/52*     (2013.01)
    *H01G 11/80*     (2013.01)
    *A23L 33/16*     (2016.01)
    *A61N 1/32*     (2006.01)
    *H01G 11/58*     (2013.01)
    *H01G 11/86*     (2013.01)
    *H02J 7/02*     (2016.01)
    *H02J 7/34*     (2006.01)

(52) U.S. Cl.
    CPC ............ *H01G 11/52* (2013.01); *H01G 11/58* (2013.01); *H01G 11/80* (2013.01); *A23V 2002/00* (2013.01); *H01G 11/86* (2013.01); *H02J 7/025* (2013.01); *H02J 7/345* (2013.01)

(56) References Cited

U.S. PATENT DOCUMENTS

| | | | |
|---|---|---|---|
| 9,047,746 B1 | 6/2015 | Euliano, II et al. | |
| 9,706,646 B2 | 7/2017 | Jiang et al. | |
| 2003/0165735 A1* | 9/2003 | Nobuta | H01G 9/10 429/153 |
| 2008/0165471 A1* | 7/2008 | Kojima | H01G 11/26 361/503 |
| 2011/0228447 A1* | 9/2011 | Gadkaree | H01G 11/26 361/502 |
| 2012/0259376 A1* | 10/2012 | Godden | A61K 9/0009 607/2 |
| 2016/0228061 A1 | 8/2016 | Kallback et al. | |
| 2017/0290151 A1 | 10/2017 | Jiang et al. | |
| 2017/0338453 A1 | 11/2017 | Yu et al. | |
| 2019/0254608 A1 | 8/2019 | Jiang et al. | |

FOREIGN PATENT DOCUMENTS

| | | | |
|---|---|---|---|
| JP | 2007335443 A * | 12/2007 | |
| WO | 2014113489 A1 | 7/2014 | |
| WO | 2016073584 A1 | 5/2016 | |
| WO | 2016109652 A1 | 7/2016 | |
| WO | 2018208989 A1 | 11/2018 | |

OTHER PUBLICATIONS

Agrawal, H. D. Espinosa, Giant piezoelectric size effects in zinc oxide and gallium nitride nanowires. A first principles investigation. Nano letters 11, 786-790 (2011).
Al-Hilli and Magnus Willander, 2009. The pH Response and Sensing Mechanism of n-Type ZnO/Electrolyte Interfaces. Sensors 9 (9), 7445.
Antipina, G. B. Sukhorukov, Remote control over guidance and release properties of composite polyelectrolyte based capsules. Adv Drug Deliv Rev 63, 716-729 (2011); published online EpubAug. 14 (10.1016/j.addr.2011.03.012).
Assaf et al., "Technical and surgical aspects of the sphenopalatine ganglion (SPG) microstimulator insertion procedure," Int. J. Oral Maxillofac. Surg., 45, 245 (2015).
Barranco, J. A. Spadaro, T. J. Berger, R. O. Becker, "In Vitro Effect of Weak Direct Current on *Staphylococcus aureus*," Clin. Orthop. Relat. Res. 100, 250-255 (1974).
Benight, C. Wang, J. B. H. Tok, Z. A. Bao, Stretchable and self-healing polymers and devices for electronic skin. Progress in Polymer Science 38, 1961-1977 (2013); published online EpubDec (10.1016/j.progpolymsci.2013.08.001).
Ben-Menachem et al., "Vagus nerve stimulation for treatment of partial seizures: 1. A controlled study of effect on seizures. First International Vagus Nerve Stimulation Study Group," Epilepsia 35, 616-626 (1994).
Bettinger, "Materials Advances for Next-Generation Ingestible Electronic Medical Devices," Trends Biotechnol. 2015, 33, 575.
Bettinger, Z. Bao, "Organic Thin-Film Transistors Fabricated on Resorbable Biomaterial Substrates," Adv. Mater. 2010, 22, 651.
Chinese Patent Office Action for Application No. 201680061026.4 dated Mar. 5, 2019 (15 pages, English translation included).
Khang, H. Q. Jiang, Y. Huang, J. A. Rogers, A stretchable form of single-crystal silicon for high-performance electronics on rubber substrates. Science 311, 208-212 (2006); published online EpubJan (10.1126/science.1121401).
Costamagna et al., A prospective trial comparing small bowel radiographs and video capsule endoscopy for suspected small bowel disease. Gastroenterology 123, 999-1005 (2002).
Cracknell, K. A. Vincent, F. A. Armstrong, Enzymes as working or inspirational electrocatalysts for fuel cells and electrolysis. Chemical Reviews 108, 2439-2461 (2008).
Davis, N. Wagle, M. D. Anderson, M. M. Warren, "Bacterial and Fungal Killing by Iontophoresis with Long-Lived Electrodes," Antimicrob. Agents Chemother. 35, 2131-2134 (1991).
Del Pozo, M. S. Rouse, J. N. Mandrekar, J. M. Steckelberg, R. Patel, "The Electricidal Effect: Reduction of *Staphylococcus* and Pseudomonas Biofilms by Prolonged Exposure to Low-Intensity Electrical Current," Antimicrob. Agents Chem. 53, 41-45 (2009).
Deuschl et al., "A randomized trial of deep-brain stimulation for parkinson's disease," N. Engl. J. Med. 355, 896-908 (2006).
Digenis, T. B. Gold, V. P. Shah, "Cross-Linking of Gelatin Capsules and Its Relevance to Their in Vitro-in Vivo Performance," J. Pharm. Sci. 1994, 83, 915.
Dorrington, D. W. Johnson, R. Brant, "The Frequency of Complications Associated With the Use of Multiple-Dose Activated Charcoal," Ann. Emergency Med. 2003, 41, 370.
EMF Portal, "Radio Frequency (10 MHz-300 GHz)," <https://web.archive.org/web/20170214032031/https://www.emf-portal.org/en/cms/page/effects-radio-frequency> webpage available at least as early as Feb. 14, 2017.
Erdman Jr. J. W., I. A. MacDonald, and S. H. Zeisel, Present Knowledge in Nutrition. (John Wiley & Sons, 2012).
Faigel, B. R. Stotland, M. L. Kochman, T. Hoops, T. Judge, J. Kroser, J. Lewis, W. B. Long, D. C. Metz, C. O'Brien, D. Smith, and G. G. Ginsberg, 1997. Device choice and experience level in endoscopic foreign object retrieval: An in vivo study. Gastrointestinal Endoscopy 43 (4), 334.
Faigel, Douglas F. Lake, Tracy L. Landreth, Catherine C. Kelman, and Ronald J. Mader, 2016. EUS-guided portal injection chemotherapy for treatment of hepatic metastases: feasibility in the acute porcine model. Gastrointestinal Endoscopy 83 (2), 444-446.
Ferris, Conducting bio-materials based on gellan gum hydrogels. Soft Matter 5, 3430-3437 (2009).
Fu, P. Y. Liu, J. Cheng, A. S. Bhalla, R. Guo, Optical measurement of the converse piezoelectric d33 coefficients of bulk and microtubular zinc oxide crystals. Applied physics letters, (2007).
Fukada, I. Yasuda, On the piezoelectric effect of bone. Journal of the physical society of Japan 12, 1158-1162 (1957).
Gao, J. D. Xu, L. E. Locascio, and C. S. Lee, 2001. Integrated microfluidic system enabling protein digestion, peptide separation, and protein identification. Analytical Chemistry 73 (11), 2648-2655.
Gennadios, et al., "Physical Properties of Egg White—Dialdehyde Starch Films," J. Agric. Food Chem. 46, 1297-1302 (1998).
Goffredo et al., A Swallowable Smart Pill for Local Drug Delivery. Journal of Microelectromechanical Systems 25, 362-370 (2016).

(56) References Cited

OTHER PUBLICATIONS

Gontard S. Marchesseau, J. L. Cuq, S. Guilbert, Water vapour permeability of edible bilayer films of wheat gluten and lipids. International journal of food science & technology 30, 49-56 (1995).
Halperin, S. Mutchnik, A. Agronin, M. Molotskii, P. Urenski, M. Salai, G. Rosenman, Piezoelectric effect in human bones studied in nanometer scale. Nano Letters 4, 1253-1256 (2004).
Hammock, A. Chortos, B. C. K. Tee, J. B. H. Tok, Z. A. Bao, 25th Anniversary Article: The Evolution of Electronic Skin (E-Skin): A Brief History, Design Considerations, and Recent Progress. Advanced Materials 25, 5997-6037 (2013); published online EpubNov (10.1002/adma.201302240).
Hong, X. Zhao, J. Zhou & Z. Suo, "A theory of coupled diffusion and large deformation in polymeric gels," J. Mech. Phys. Solids 56, 1779-1793 (2008).
Huang et al., Biodegradable materials for multilayer transient printed circuit boards. Advanced Materials 26, 7371-7377 (2014).
Huggins, "Solutions of Long Chain Compounds," J. Chem. Phys. 9, 440-440 (1941).
Hwang, et al., "A Physically Transient Form of Silicon Electronics," Science 337, 1640-1644 (2012).
Hwang, et al., "Biodegradable Elastomers and Silicon Nanomembranes/Nanoribbons for Stretchable, Transient Electronics, and Biosensors," Nano Lett. 15, 2801-2808 (2015).
Hwang, et al., "High-Performance Biodegradable/Transient Electronics on Biodegradable Polymers," Adv. Mater. 26, 3905-3911 (2014).
International Preliminary Report on Patentability for Application No. PCT/US2016/048602 dated Mar. 8, 2018 (9 pages).
International Search Report and Written Opinion for Application No. PCT/US2016/048602 dated Nov. 21, 2016 (10 pages).
International Search Report and Written Opinion for Application No. PCT/US2019/18785 dated Apr. 30, 2019 (14 pages).
Irimia-Vladu, ""Green" electronics: biodegradable and biocompatible materials and devices for sustainable future," Chem. Soc. Rev. 2014, 43, 588.
Irimia-Vladu, E. D. Glowacki, G. Voss, S. Bauer, N. S. Sariciftci, "Green and biodegradable electronics," Mater. Today 15, 340-346 (2012).
Irimia-Vladu, et al., "Biocompatible and Biodegradable Materials for Organic Field-Effect Transistors," Adv. Funct. Mater. 20, 4069-4076 (2010).
Irimia-Vladu, et al., "Indigo—A Natural Pigment for High Performance Ambipolar Organic Field Effect Transistors and Circuits," Adv. Mater. 24, 375 (2012).
Kahlon, M. Chapman, G. Smith, In vitro binding of bile acids by spinach, kale, brussels sprouts, broccoli, mustard greens, green bell pepper, cabbage and collards. Food chemistry 100, 1531-1536 (2007).
Kang, et al., "Biodegradable Thin Metal Foils and Spin-On Glass Materials for Transient Electronics," Adv. Funct. Mater. 25, 1789-1797 (2015).
Karimi, M. Navidbakhsh, H. Yousefi & M. Alizadeh, "An experimental study on the elastic modulus of gelatin hydrogels using different stress—strain definitions," Journal of Thermoplastic Composite Materials, 2014.
Kavanagh, T. Menand & K. A. Daniels, "Gelatine as a crustal analogue: Determining elastic properties for modelling magmatic intrusions," Tectonophysics 582, 101-111 (2013).
Kim, J. H. Ahn, W. M. Choi, H. S. Kim, T. H. Kim, J. Z. Song, Y. G. Y. Huang, Z. J. Liu, C. Lu, J. A. Rogers, Stretchable and foldable silicon integrated circuits. Science 320, 507-511 (2008); published online EpubApr (10.1126/science.1154367).
Kim, R. Ghaffari, N. S. Lu, J. A. Rogers, "Flexible and stretchable electronics for biointegrated devices," in Annual Review of Biomedical Engineering, vol. 14, M. L. Yarmush, Ed. (2012), vol. 14, pp. 113-128.
Kim, S. Yun, Z. Ounaies, Discovery of cellulose as a smart material. Macromolecules 39, 4202-4206 (2006).
Kim, S.-E. Chun, J. Whitacre, C. J. Bettinger, "Self-deployable current sources fabricated from edible materials," J. Mater. Chem. B 1, 3781-3788 (2013).
Kim, W. Wu, S. E. Chun, J. F. Whitacre, C. J. Bettinger, Catechol-Mediated Reversible Binding of Multivalent Cations in Eumelanin Half-Cells. Advanced Materials 26, 6572-6579 (2014).
Kim, W. Wu, S.-E. Chun, J. F. Whitacre, C. J. Bellinger, "Biologically derived melanin electrodes in aqueous sodium-on energy storage devices," Proc. Natl. Acad. Sci. U.S.A. 110, 20912-20917 (2013).
Koziolek et al., Investigation of pH and temperature profiles in the GI tract of fasted human subjects using the Intellicap® system. Journal of pharmaceutical sciences 104, 2855-2863 (2015).
Kroin et al., Long-term testing of an intracranial pressure monitoring device. Journal of neurosurgery 93, 852-858 (2000).
Król, A. Jarmoluk, "The effects of using a direct electric current on the chemical properties of gelatine gels and bacterial growth," J. Food Eng. 170, 1-7 (2016).
Lee, J. Shim, and H. G. Lee, 2004. Mechanical properties of gellan and gelatin composite films. Carbohydrate Polymers 56 (2), 251-254.
Li, D. Young, K. Xiang, W. C. Carter, Y.-M. Chiang, "Towards High Power High Energy Aqueous Sodium-Ion Batteries: The NaTi2 (PO4)3/Na0.44MnO2 System," Adv. Energy Mater. 3, 290-294 (2013).
Li, R. S. Yang, M. Yu, F. Bai, C. Li, and Z. L. Wang, 2008. Cellular Level Biocompatibility and Biosafety of ZnO Nanowires. Journal of Physical Chemistry C 112 (51), 20114-20117.
Li, V. Kothari, B. S. Terry, Design and Preliminary Experimental Investigation of a Capsule for Measuring the Small Intestine Contraction Pressure. IEEE Transactions on Biomedical Engineering 62, 2702-2708 (2015).
Lipomi, M. Vosgueritchian, B. C. K. Tee, S. L Hellstrom, J. A. Lee, C. H. Fox, Z. N. Bao, Skin-like pressure and strain sensors based on transparent elastic films of carbon nanotubes. Nature Nanotechnology 6, 788-792 (2011); published online EpubDec (10.1038/nnano.2011.184).
Lu, T. Chen, "Application of egg white and plasma powders as muscle food binding agents," J. Food Eng. 42, 147-151 (1999).
Marino, R. O. Becker, Piezoelectricity in hydrated frozen bone and tendon. Nature 253, 42 (1975).
Matsunaga, et al., "Disinfection of Drinking Water by Using a Novel Electrochemical Reactor Employing Carbon-Cloth Electrodes," Appl. Environ. Microbiol. 58, 686-689 (1992).
Matsunaga, S. Nakasono, S. Masuda, "Electrochemical sterilization of bacteria adsorbed on granular activated carbon," FEMS Microbiol. Lett. 72, 255-259 (1992).
Munoz, G. Alici, W. Li, A review of drug delivery systems for capsule endoscopy. Adv Drug Deliv Rev 71, 77-85 (2014).
Nathan, S. Center, C.-y. Wu, W. Keller, An implantable synchronous pacemaker for the long term correction of complete heart block. The American journal of cardiology 11, 362-367 (1963).
Neuvonen, "Clinical Pharmacokinetics of Oral Activated Charcoal in Acute Intoxications," Clin. Pharmacokinet. 1982, 7, 465.
Neuvonen, K. T. Olkkola, "Oral Activated Charcoal in the Treatment of Intoxications," Med. Toxicol. Adverse Drug Exper. 1988, 3, 33.
Ofner, Y. E. Zhang, V. C. Jobeck, B. J. Bowman, "Crosslinking Studies in Gelatin Capsules Treated with Formaldehyde and in Capsules Exposed to Elevated Temperature and Humidity," J. Pharm. Sci. 2001, 90, 79.
Parker, P. Domachuk, J. Amsden, J. Bressner, J. A. Lewis, D. L. Kaplan, F. G. Omenetto, Biocompatible silk printed optical waveguides. Advanced Materials 21, 2411-2415 (2009).
Peng et al., Diagnosing lung cancer in exhaled breath using gold nanoparticles. Nature nanotechnology 4, 669-673 (2009).
Pickup, H. Keen, "Continuous Subcutaneous Insulin Infusion at 25 Years," Diabetes Care 25, 593-598 (2002).
Qureshi, Current and future applications of the capsule camera Nature reviews drug discovery 3, 447-450 (2004).
Ramuz, B. C. K. Tee, J. B. H. Tok, Z. N. Bao, Transparent, Optical, Pressure-Sensitive Artificial Skin for Large-Area Stretchable Elec-

(56) References Cited

OTHER PUBLICATIONS tronics. Advanced Materials 24, 3223-3227 (2012); published online EpubJun (10.1002/adma.201200523).

Reinish, A. S. Nowick, Piezoelectric properties of bone as functions of moisture content. (1975).

Rogers, T. Someya, Y. G. Huang, Materials and Mechanics for Stretchable Electronics. Science 327, 1603-1607 (2010); published online EpubMar (10.1126/science.1182383).

Ross, C. L. Taylor, A. L. Yaktine, and H. B. Del Valle, Dietary Reference Intakes for Calcium and Vitamin D. (National Academies Press, 2011).

Rossi, C. L. Dias, E. M. Donato, L. A. Martins, A. M. Bergold, and P. E. Froeehlich, 2007. Development and validation of dissolution test for ritonavir soft gelatin capsules based on in vivo data. International Journal of Pharmaceutics 338 (1-2), 119-124.

Sandvik, B. R. McLeod, A. E. Parker, P. S. Stewart, Direct electric current treatment under physiologic saline conditions kills *Staphylococcus epidermidis* biofilms via electrolytic generation of hypochlorous acid. PloS one 8, (2013).

Schubert, 2014. Gastric secretion. Current Opinion in Gastroenterology 30 (6), 578-582.

Siegel, K. Church, G. Schmidt, "Gel Structure of Nonmeat Proteins as Related to Their Ability to Bind Meat Pieces," J. Food Sci. 44, 1276-1279 (1979).

Tamborlane, R. S. Sherwin, M. Genel, P. Felig, "Reduction to normal of plasma glucose in juvenile diabetes by subcutaneous administration of insulin with a portable infusion pump," N. Engl. J. Med. 300, 573-578 (1979).

Tao, D. L. Kaplan, F. G. Omenetto, "Silk Materials—A Road to Sustainable High Technology," Adv. Mater. 2012, 24, 2824.

Vanin, P. J. A. Sobral, F. C. Menegalli, R. A. Carvalho, and Amqb Habitante, 2005. Effects of plasticizers and their concentrations on thermal and functional properties of gelatin-based films. Food Hydrocolloids 19 (5), 899-907.

Vosgueritchian, D. J. Lipomi, Z. A. Bao, Highly Conductive and Transparent PEDOT:PSS Films with a Fluorosurfactant for Stretchable and Flexible Transparent Electrodes. Advanced Functional Materials 22, 421-428 (2012); published online EpubJan (10.1002/adfm.201101775).

Wang, W. Xu, P. Chatterjee, C. Lv, J. Popovich, Z. Song, L. Dai, M. Y. S. Kalani, S. E. Haydel, H. Jiang, Food-Materials-Based Edible Supercapacitors. Advanced Materials Technologies 1, (2016).

Welz, C. M. Ofner, "Examination of Self-Crosslinked Gelatin as a Hydroggel for Controlled Release," J. Pharm. Sci. 1992, 81, 85.

Wu, A. Mohamed, J. F. Whitacre, "Microwave Synthesized $NaTi_2(PO_4)_3$ as an Aqueous Sodium-Ion Negative Electrode," J. Electrochem. Soc. 160, A497-A504 (2013).

Wu, M. Khdour, P. Apsangi, and H. Yu, 2017. High-Frequency Magnetic Thin-Film Inductor Integrated on Flexible Organic Substrates. IEEE Transactions on Magnetics 53 (11), 1-7.

Xu et al. "Food Based Edible and Nutritive Electronics" Advanced Materials Technologies, 2017 (10.1002/admt.201700181).

Xu, Y. H. Zhang, L. Jia, K. E. Mathewson, K. I. Jang, J. Kim, H. R. Fu, X. Huang, P. Chava, R. H. Wang, S. Bhole, L. Z. Wang, Y. J. Na, Y. Guan, M. Flavin, Z. S. Han, Y. G. Huang, J. A. Rogers, Soft Microfluidic Assemblies of Sensors, Circuits, and Radios for the Skin. Science 344, 70-74 (2014); published online EpubApr (10.1126/science.1250169).

Yan, Q. Wang, T. Wei, Z. Fan, "Recent Advances in Design and Fabrication of Electrochemical Supercapacitors with High Energy Densities," Adv. Energy Mater. 2014, 4, 4.

Yin, et al., "Materials, Designs, and Operational Characteristics for Fully Biodegradable Primary Batteries," Adv. Mater. 26, 3879-3884 (2014).

Zhang, X. Zhao, "Carbon-based materials as supercapacitor electrodes," Chem. Soc. Rev. 38, 2520-2531 (2009).

\* cited by examiner

| BINDER | CURRENT COLLECTOR | ELECTROLYTE | SEPARATOR | SEGREGATION LAYER | PACKAGE |
|---|---|---|---|---|---|
| Egg | Au | Gatorade+MSG | Seaweed | Cheese | Gelatin |
| Egg | Au | Monster drink | Rice Paper | Cheese | Gelatin |
| CMC | Au | V8 drink | Seaweed | Cheese | Gummy Candy |
| Egg | Ag | BBQ Sauce | Seaweed | --- | Gelatin |
| CMC | Au | Jello | --- | --- | Gummy Candy |
| CMC | Ag | Cheese | --- | --- | Gummy Candy |

EDIBLE SUPERCAPACITORS

RELATED APPLICATIONS

This application claims the benefit of U.S. Provisional Patent Application Nos. 62/209,695, filed Aug. 25, 2015, and 62/292,625, filed Feb. 8, 2016, the entire contents of both of which are incorporated herein by reference.

BACKGROUND

The present invention relates to supercapacitors and methods for manufacturing supercapacitors for use in medical device applications. According to a report from EvaluateP-harma, the global medical device market will reach $440 billion by 2018. Many of these devices, such as deep brain neurostimulators, cardiac defibrillators, pacemakers and insulin pumps, require an embedded energy source.

SUMMARY

Batteries, especially Li-ion batteries, are widely used as medical device power sources. However, batteries generally contain toxic metals (e.g., lithium, lead, or cadmium) as well as many other toxic organic components in the electrolyte. Also, because of limitations relating to their internal electrochemical properties, batteries are generally not suitable for some special cases such as outputting high frequency impulses or high instantaneous power.

In various embodiments, this invention provides a very clean, non-toxic mechanism for manufacturing supercapacitors, specifically electric double-layer capacitors, that are able to accept and deliver charge much faster than batteries and tolerate a greater number of charge and discharge cycles. Various examples are provided in this disclosure for the fabrication of a novel symmetrical edible electric double-layer capacitor made entirely out of food.

In one embodiment, the invention provides a capacitive power source that includes an anode electrode, an anode current collector, a cathode electrode, and a cathode current collector, arranged in layers with a separator layer positioned between the anode electrode and the cathode electrode forming a symmetrical electrical double-layer capacitor. The anode electrode, the anode current collector, the cathode electrode, the cathode current collector, and the separator layer are all constructed of non-toxic, edible materials. In some such embodiments, the layered arrangement is enclosed in a packaging material with a conductive anode tab and a conductive cathode tab extending from the packaging material. The conductive anode tab is coupled to the anode current collector and the conductive cathode tab is coupled to the cathode current collector. The packaging material, the conductive anode tab, and the conductive cathode tab are all also constructed of non-toxic, edible materials forming a completely edible capacitive power source package.

In some embodiments, the invention provides a supercapacitor that includes activated charcoal (e.g., from dietary supplement capsules) as the electrode material. Slurries are prepared by mixing the activated charcoal with egg white. A 23 kt edible gold leaf material is used as a current collector and unbleached cellulose paper is attached at the back of the thin gold leaf for supporting purposes. Egg white is also used as a binder between the gold leaf and the cellulose paper. Roasted seaweed—for example, the type generally used for sushi, is used as a separator and gelatin sheet is used as a package material. An electrolyte drink, such as GATORADE®, which contains 0.02 mol/L sodium ion and 0.003 mol/L potassium ion, is used as an electrolyte.

In some examples, the edible, food-based supercapacitors exhibit antibacterial activity capable of killing bacteria in vitro and are sufficiently powerful to drive a commercial snake camera with wireless charging capabilities. By storing electric charges in food, these systems demonstrate that properly assembled food materials can function as biomedical devices.

Other aspects of the invention will become apparent by consideration of the detailed description and accompanying drawings.

DETAILED DESCRIPTION

Before any embodiments of the invention are explained in detail, it is to be understood that the invention is not limited in its application to the details of construction and the arrangement of components set forth in the following description or illustrated in the following drawings. The invention is capable of other embodiments and of being practiced or of being carried out in various ways.

Novel and innovative medical technologies and devices have emerged to treat various diseases, such as deep brain stimulators for Parkinson's diseases, vagal nerve stimulators for epilepsy, electronic aspirin for head or facial pains, and insulin pumps for diabetes, among others. Although implantable electronic devices have revolutionized the care of patients, they harbor shortcomings such as the need for operations and perioperative complications associated with an operation, battery changes, and revisions from time to time. Biodegradable electronics and bioresolvable devices, such as individual transistors, primary battery and biosensors, and organic field effect transistors, might provide an alternative option to implantable electronics. Although biodegradable electronics might resolve the issue of repeat surgery, they may introduce other inherent shortcomings, such as limitations with structural materials and properties.

In addition to implantation of permanent and biodegradable devices, the digestive system may serve as another route for administration of electronics that can modulate cellular and organ function without the need for implantation. With the use of capsule endoscopy, electronic devices could pass through the digestive tract and modulate its function.

The systems and methods described in this disclosure bridge the food industry, material sciences, device fabrication, and biomedical engineering by demonstrating fully functional and edible supercapacitors, a type of energy source that can be used in electronics. In some implementations, all of the materials involved in generating the supercapacitor package are explicitly originated from edible and nontoxic food products, including, for example, activated charcoal, seaweed, polyelectrolyte drink, rice paper, egg, gold leaf, cooking sauces, collagen-based candy, and cheese. In some implementations, these edible supercapacitors also exhibit in vitro antibacterial activity and are capable of powering an endoscopic "snake" camera with wireless charging capability.

Figures 1A, 1B:
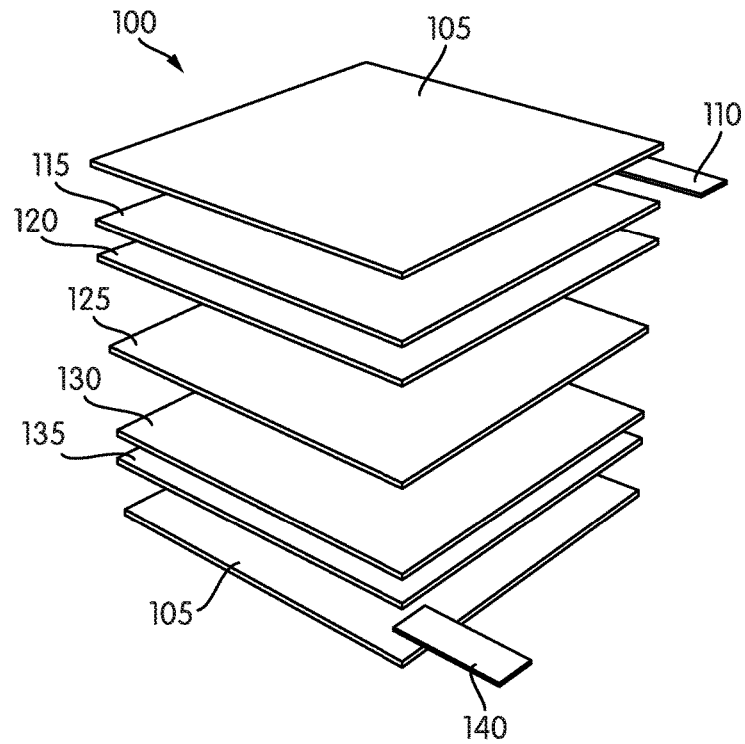
FIG. 1A is an exploded view of a supercapacitor according to one embodiment.
FIG. 1B is a table listing potential non-toxic, edible materials that could be used to construct the various components of the supercapacitor of FIG. 1A.

FIG. 1A illustrates an exploded view of a layered supercapacitor device 100. The supercapacitor 100 includes a packaging material 105 at the top and bottom of the device 100. In some implementations, as discussed in further detail below, the packing material 105 at the top and bottom of the device 100 are sealed together to enclose the other layers of the device 100 and to provide a sealed supercapacitor package. An anode conductive tab 110 is sandwiched between the packaging material layer 105 and an anode current collector layer 115 or, in some implementations, the anode conductive tab 105 is provided as part of the anode current collector layer 115. Similarly, a cathode conductive tab 140 is sandwiched between the packaging material layer 105 and a cathode current collector layer 135 or, in some implementations, the cathode conductive tab 140 is provided as part of the cathode current collector layer 135. A first electrode layer 120 and a second electrode layer 130 are positioned between the anode current collector layer 115 and the cathode current collector layer 135 and are separated by a separator layer 125.

The electrode layers 120, 130 may be constructed of a conductive and porous material such as activated charcoal, copper, magnesium, and gold or silver powder paste. In some implementations, the electrode layers 120, 130 are provided by combining an electrode material (e.g., activated charcoal) with a binder such as egg white to create a slurry. The anode current collector layer 115 and cathode current collector layer 135 must be conductive and can include, for example, gold or silver leaf/foil. The separator layer 125 includes a porous insulator material and can be constructed, for example, of seaweed, air-dried meat, rice paper, pork casing, sugar sheet, vegetable paper, wafer paper (made from potato starch), or Tapioca paper. The packaging material layer 105 is generally insulating and can be provided as gelatin, potato starch, soy lecithin paper, edible waxed paper/film, or another edible film. Gummy drops, gum, or dough may also be used as a packaging material, but may require further processing. One or more of these layers may be coupled together using a sticky binding material such as, for example, egg, egg powder, sugar, GellanGun, starch, honey, extract juice from sticky food (e.g., okra or chinesevam), or carboxymethyl cellulose (CMC) (i.e., cellulose gum). In some implementations, as discussed further below, an electrolyte material may also be included within the semiconductor device 100 package. The electrolyte material contains ions and can be provided, for example, as phosphate buffered saline (PBS), an electrolytic drink such as GATORADE, lemonade, coconut water, vegetable juice (e.g., V8®), gel electrolytes (e.g., barbeque sauce), JELL-O®, or cheese. FIG. 1B illustrates a table of various possible food-based materials that can be used to provide layers/components of the supercapacitor device 100 illustrated in FIG. 1a.

Figure 2:
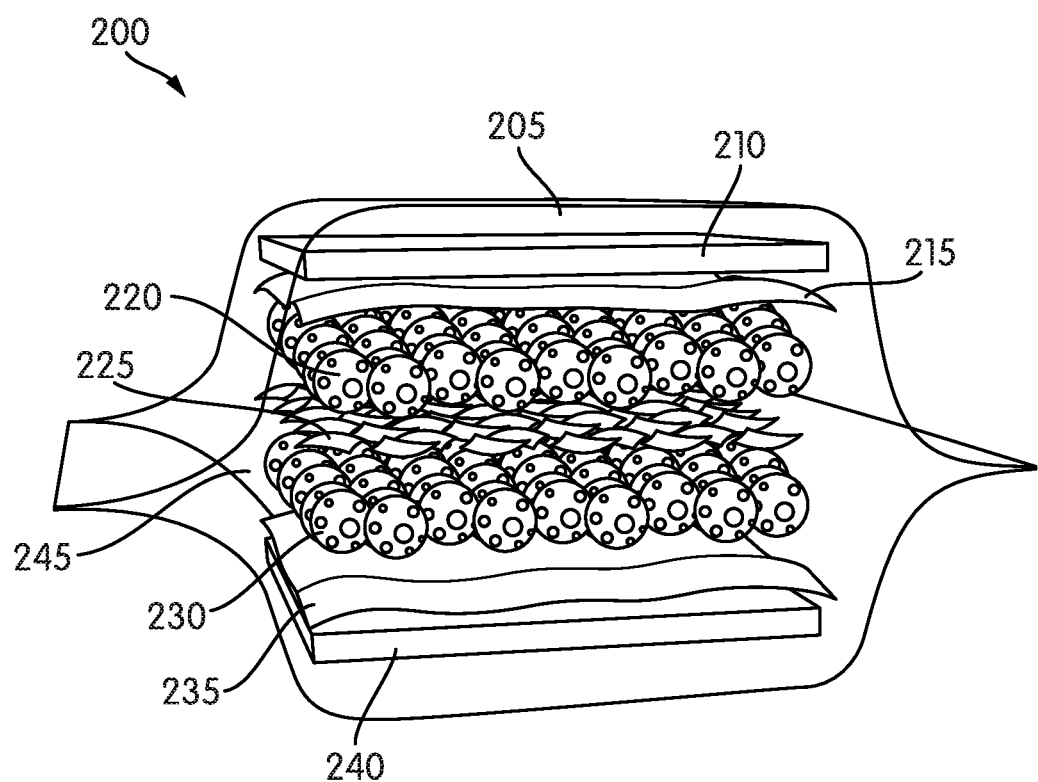
FIG. 2 is a cross-sectional view of a specific example of a supercapacitor according to FIG. 1A.

FIG. 2 illustrates a specific example of a supercapacitor 200 constructed according to the example of FIG. 1A. All components of the supercapacitor 200 of FIG. 2 originate from food. A first segregation layer of cheese 210 and a second segregation layer of cheese 240 are provided to separate the active supercapacitor materials from a gelatin package 205. A first current collector layer 215 and a second current collector layer 235 are gold leaf, a first electrode 220 and a second electrode 230 comprise activated charcoal, a separator 225 is seaweed, and the electrolyte 245 is Gatorade. The gelatin package 205 is sealed to encase the active supercapacitor materials and to provide a sealed, edible supercapacitor device 200. Electrical power is drawn from the supercapacitor 200 by coupling an electronic device (e.g., a swallowable, capsule-based medical device) to the anode conductive tab and the cathode conductive tab (not shown in FIG. 2) protruding from the gelatin package 205.

In order to bind discrete activated charcoal particles into a continuum film as electrodes, edible binders are employed. In particular, egg whites were used as binders in the electrodes 220, 230 of the example of FIG. 2. The presence of hydrogen bonds and ionic interactions with proteins allows the formation of films with high adhesive strength, which allows egg whites to be used as binders in food processing industries. The electrodes 220, 230 of the supercapacitor 200 was prepared by mixing activated charcoal (Nature's Way Products, Inc; Green Bay, Wis.) with a quantity of egg white in a mass ratio of 1:2. Egg whites primarily contain biotin and proteins such as albumin, mucoproteins, and globulins that are able to form a biomacromolecule solution with water through hydrogen bonding between the proteins and water. Deionized water was then added into the mixture with a ratio of 1:3 (activated charcoal to water). The mixture was magnetic stirred for 2 hours followed by an ultrasonication for 30 minutes in water bath. The electrodes 220, 230 in this particular example are 2 cm×2 cm and are approximately 120 μm thick. However, other sizes and thicknesses are possible based on the design and power-requirements of the medical device to be powered by the supercapacitor 200.

Figure 3A:
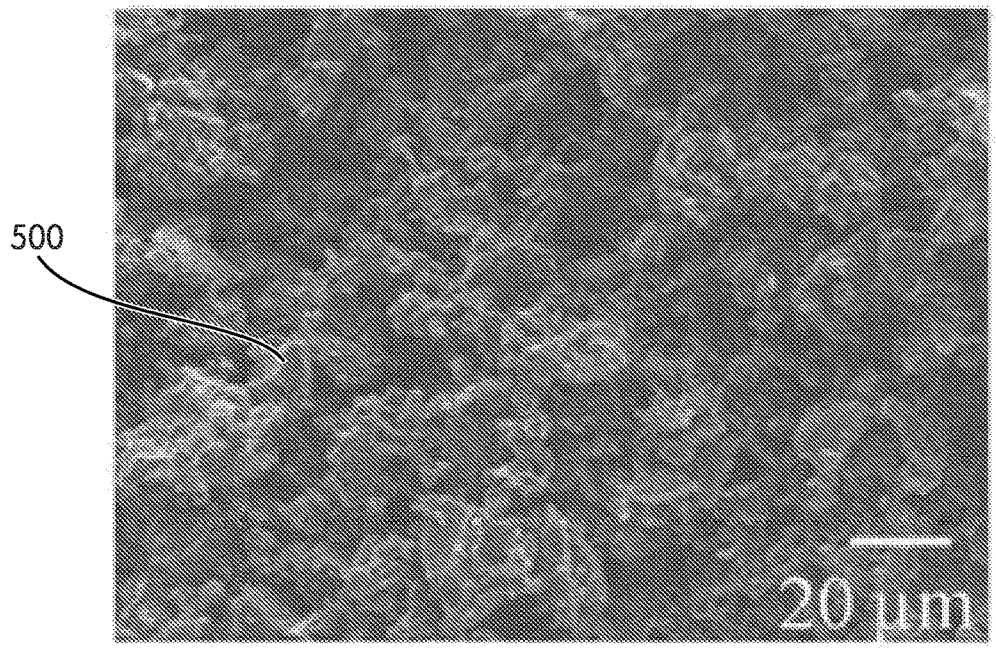
FIG. 3A is a SEM image of the relative particle size and porous structure of the activated charcoal material in the supercapacitor of FIG. 2.
Figure 3B:
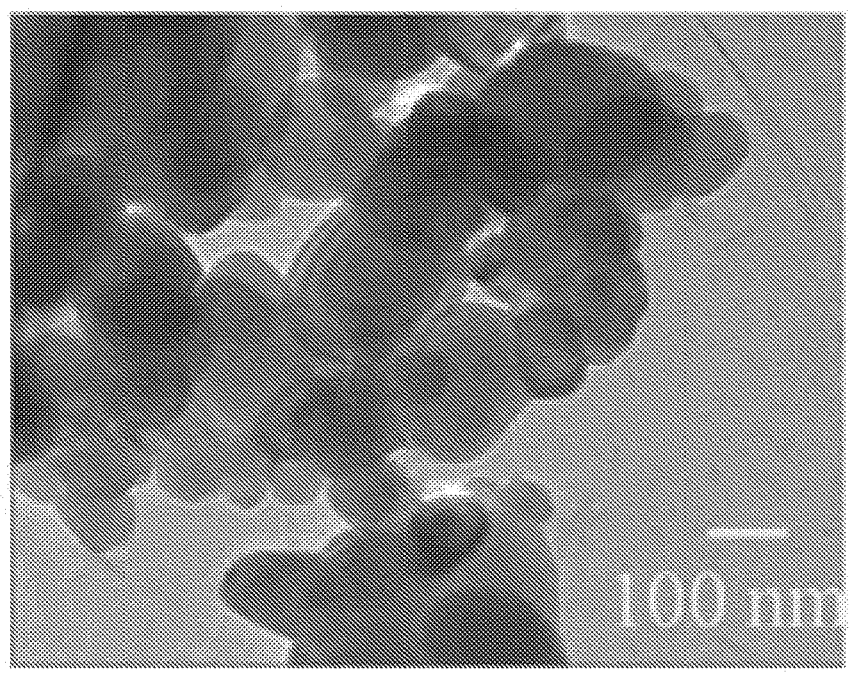
FIG. 3B is a TEM image of the relative particle size of the activated charcoal material in the supercapacitor of FIG. 2.
Figure 4:
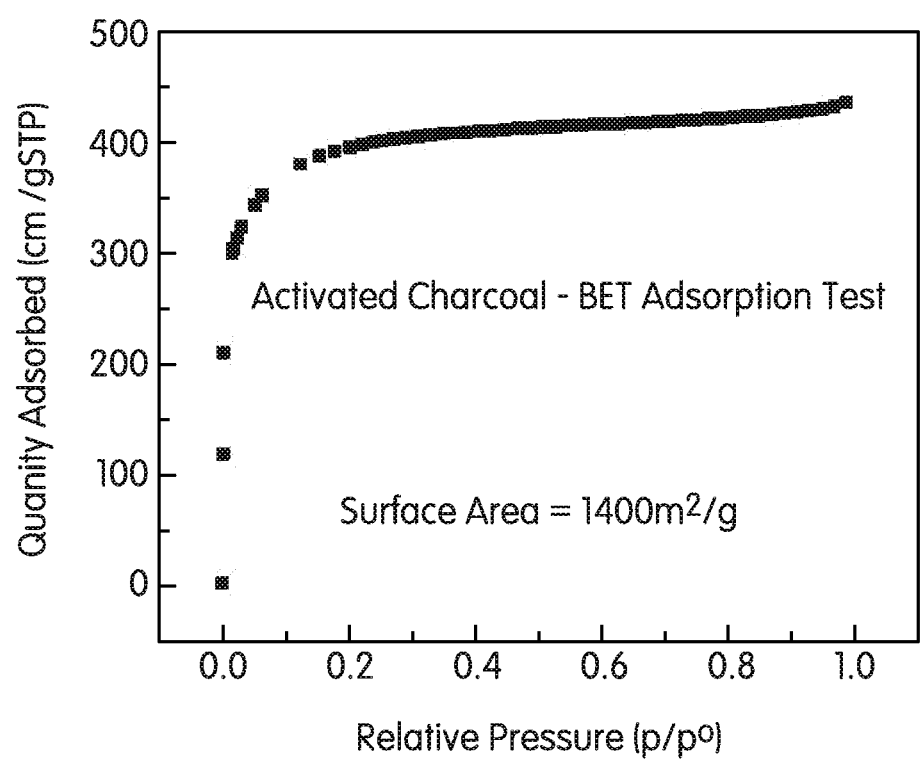
FIG. 4 is a graph demonstrating the output of a Brunauer-Emmett-Teller (BET) test demonstrating the surface area of the activated charcoal material of FIGS. 3A and 3B.

FIG. 3A shows the activated charcoal used for the electrode 220, 230 under scanning electron microscope (SEM) and FIG. 3B shows the electrode 220,230 under transmission electrode microscope (TEM). These figures demonstrate that the carbon cluster is highly porous and the size of individual carbon particles is about 100 nm. Therefore, this form of carbon provides a high electrode surface area for the supercapacitor 200. FIG. 4 illustrates a graph demonstrating the output of a Brunauer-Emmett-Teller (BET) test demonstrating the surface area of the activated charcoal 500 used in the electrodes 220 and 230 of FIGS. 3A and 3B. The surface area of the activated charcoal is approximately 1,400 $m^2/g$, which is comparable to activated carbon materials used in other, non-edible supercapacitor devices.

Edible metals, such as very thin gold and silver leaf that are used in artisan baking and many Eastern cuisines, may be used as current collector layers 215 and 235 in the supercapacitor 200. The sheet resistance of gold leaf with a thickness of 3-5 μm was measured to be 0.48 Ω/sq by four-point probe. The gold leaf material used in the supercapacitor 200 has a thickness of 120 μm and other thicknesses may be used in other implementations. In the specific example of FIG. 2, the first and second current collectors 215 and 235 were prepared by applying egg white uniformly on a chlorine-free wood fiber paper (Mondi; Graz-Seiersberg, Austria) to form an adhesive layer, then attaching an approximately 3 μm thick 23 kt edible gold leaf (Alma Gourmet Ltd; Long Island City, N.Y.) on the paper. The gold-coated paper was then dried in ambient environment for 2 hours before being patterned into the first and second current collectors 215 and 235 with desired areas. The mixture was coated on the first and second current collectors 215 and 235 by doctor's blading followed by overnight drying in an ambient environment and 6 hours drying in a room temperature, low pressure (10 Pa) chamber to avoid thermal stress as well as remove the water in the electrode.

The materials of the separator 225 is permeable to ions while also displaying high electrical resistance to avoid electrical contact between the electrodes 220, 230 of the supercapacitor 200. Roasted seaweed (Nagai NoRi Co., Ltd; Torrance, Calif.)—a popular snack and also heavily used in sushi, with multilayer hydrophilic structures—is used as the separator 225 in the example of FIG. 2. Seaweed consists of multilayer hydrophilic structures with high electrical resistivity and high ion permeability. In other implementations, rice paper might be used as the separator 225 with similar results. The seaweed and rice paper were studied for their permittivity using deionized water as the passing fluid. Two-inch diameter sections of seaweed and rice paper were cut out using a circular stamp. The testing material (i.e., seaweed and rice paper) was placed at the end of a 5-inch steel chamber using a rubber gasket. Water was poured into the chamber, and the sequential pressure test was performed using regulated nitrogen from a cylinder. The fluid passing out from the chamber was collected in a beaker and placed on a weighing balance, which was connected to a computer. The data from the fluid pass was used to calculate mass flux and permittivity. The permittivity of the roasted seaweed was measured to be 52 $g/m^2s$.

Figure 5:
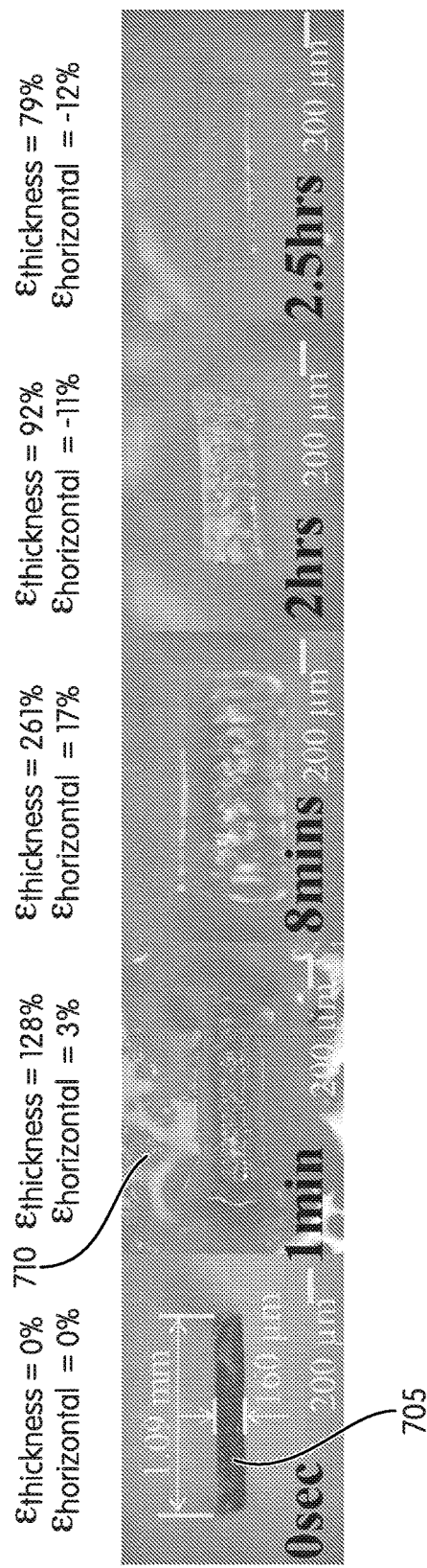
FIG. 5 is a series of overhead images of the gelatin packaging material of the supercapacitor of FIG. 2 in a simulated gastric fluid over time during a dissolution test.
Figure 6:
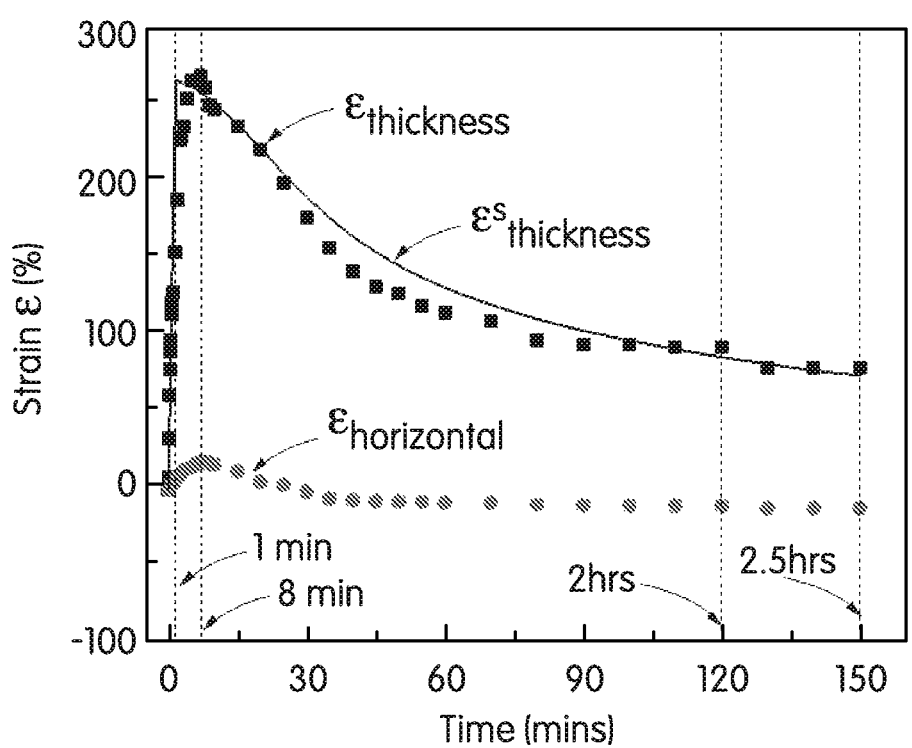
FIG. 6 is a graph of the time evolutions of strains of the supercapacitor of FIG. 2.

Gelatin sheets (Modernist Pantry, LLC; York, Me.)—such as used in food processes and medical capsules—are employed as the packaging layer 205 in the example of FIG. 2. FIG. 5 illustrates a cross-sectional view of an in-situ observation of a digestion process when a gelatin sheet 705 is immersed in a simulated gastric fluid 710 and constrained in the horizontal direction. It is observed that the gelatin sheet 705 with an initial cross-sectional area of 160 μm by 1,090 μm first swells due to the diffusion of the gastric fluid 710 into the polymeric gelatin network, and then shrinks due to the digestion of the gelatin sheet 705 and eventually becomes undetectable microscopically (using a Nikon Eclipse 1v100 with a 5× objective in the example of FIG. 5) after 2.5 hours. During this process, because of the constraint in the horizontal direction, the maximum strain in the horizontal direction ($\varepsilon_{horizontal}$) is only 17% while its counterpart in the thickness direction ($\varepsilon_{thickness}$) is 261%. This quasi-one-dimensional constrained digestion process can be understood by a theoretical model that considers the coupling of mass diffusion, chemical reaction, and extremely large mechanical deformation. As shown in FIG. 6, the time evolutions of the strains ($\varepsilon_{horizontal}$ and $\varepsilon_{thickness}$) obtained from experiments and simulations agree very well.

A polyelectrolytic drink, such as GATORADE, with high concentrations of sodium, potassium, citrate, and other stabilizing agents and high ionic conductivity (>2 mS/cm) was used as the electrolyte 245 in the example of FIG. 2. Cheese slices (Lucerne Foods, Inc.; Pleasanton, Calif.) are positioned as a segregation layer 210, 240 between the highly hydrophilic gelatin sheet (package layer 205) and the gold leaf current collectors 215 and 235 to avoid direct contact between the gelatin sheet package layer 205 and the electrolyte 245—and, thereby, preventing absorption of the electrolyte by the gelatin package 205. Finally, the package 205 is sealed thermally by an impulse sealer with controlled heat. Thus, an entirely edible supercapacitor is assembled using only food items.

Figure 7:
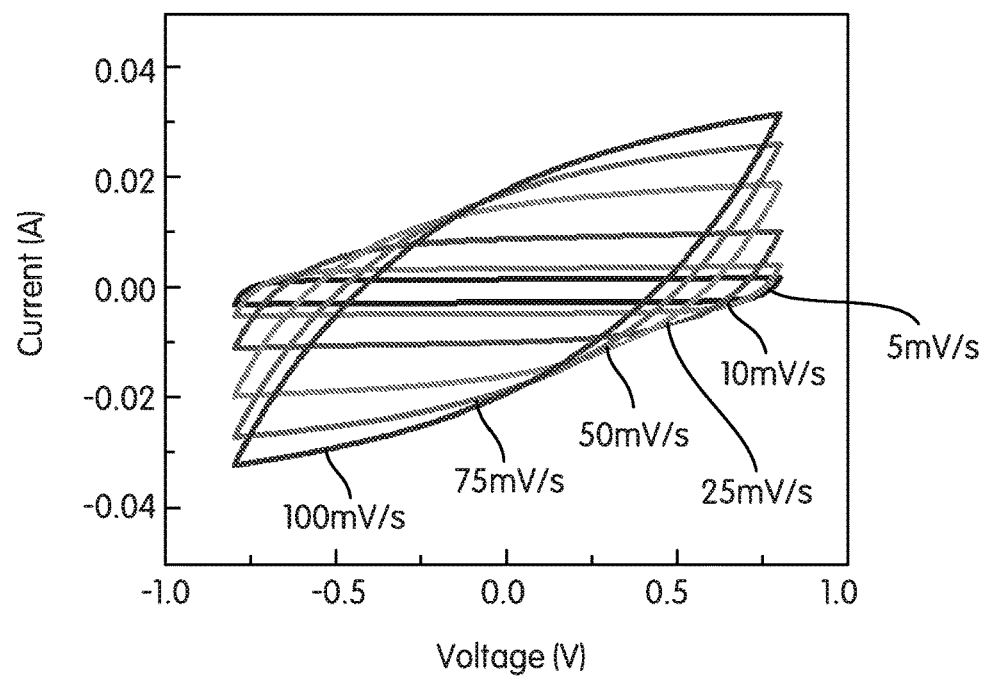
FIG. 7 is a graph of the CV curves for the supercapacitor of FIG. 2 at scan rates from 5 mV/s to 100 mV/s.
Figure 8:
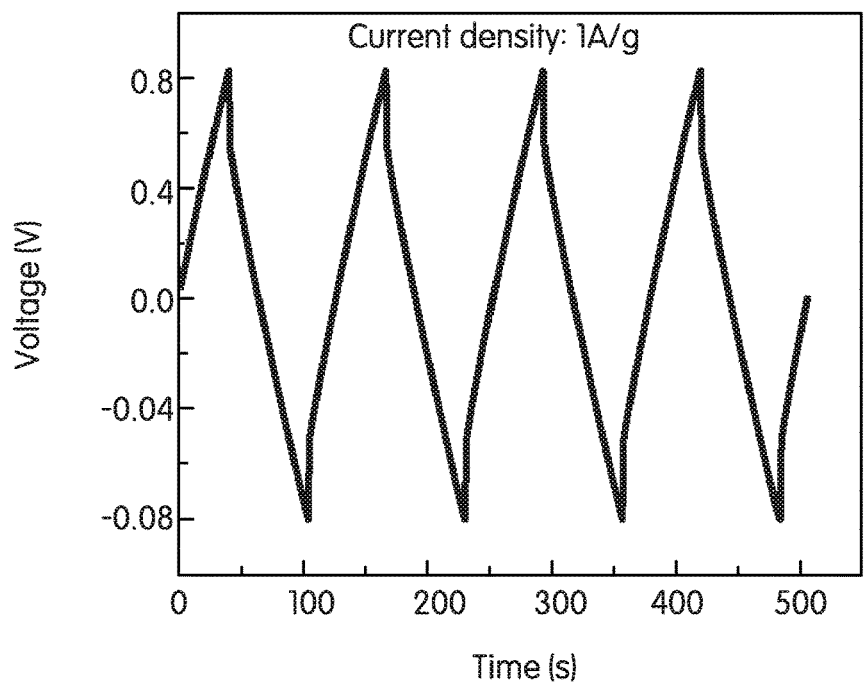
FIG. 8 is a graph of voltage as a function of time during galvanostatic charge-discharge cycles for the supercapacitor of FIG. 2.

FIG. 7 illustrates the cyclic voltammetry (CV) curves of the edible supercapacitor 200 of FIG. 2 at scanning rates from 5 mV/s to 100 mV/s. The CV curves are of clearly rectangular shape at lower scanning rates and become approximately rectangular shape at increased scanning rates, which are ideal for capacitive properties and reversibility of a supercapacitor 200. The galvanostatic charge/discharge testing results are illustrated in FIG. 8 and show some internal resistance with a constant current density of 1 A/g.

Figure 9:
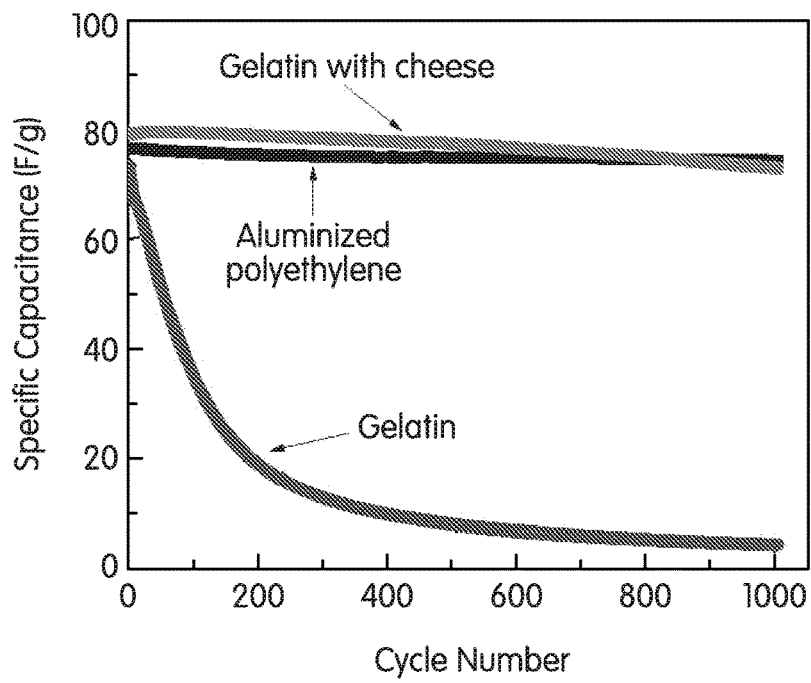
FIG. 9 is a graph of the specific capacitance of the supercapacitor of FIG. 2 for each cycle during the Galvanostatic charge-discharge cycles of FIG. 9.

As illustrated in FIG. 9, after 1,000 charge/discharge cycles, the specific capacitance retains 92.3% dropping from 78.8 F/g to 72.7 F/g under 1 A/g current density, which is consistent with activated carbon-based supercapacitors. The specific capacitance (Csp) was calculated from the slope of the discharge capacitance Csp=2I/(m(ΔV/Δt)), where I is the applied current and m is the average mass of the two electrodes. The degradation mainly results from the electrolyte being absorbed by the gelatin sheet. To confirm, aluminized polyethylene (PE) (standard packing materials for supercapacitors) and gelatin without cheese segregation were tested for comparison. The specific capacitance using aluminized PE retains 96.9% by dropping from 76.4 F/g to 74.0 F/g after 1,000 charge/discharge cycles and thus demonstrates excellent electrochemical stability of the electrode-separator-electrolyte system. However, the specific capacitance with gelatin drops more than 50% from 73.2 F/g to less than 34.9 F/g in 100 cycles and to 4.4 F/g in 1,000 cycles. This comparison shows that cheese slices can significantly prevent electrolyte loss and improve the cycling stability.

Figure 10:
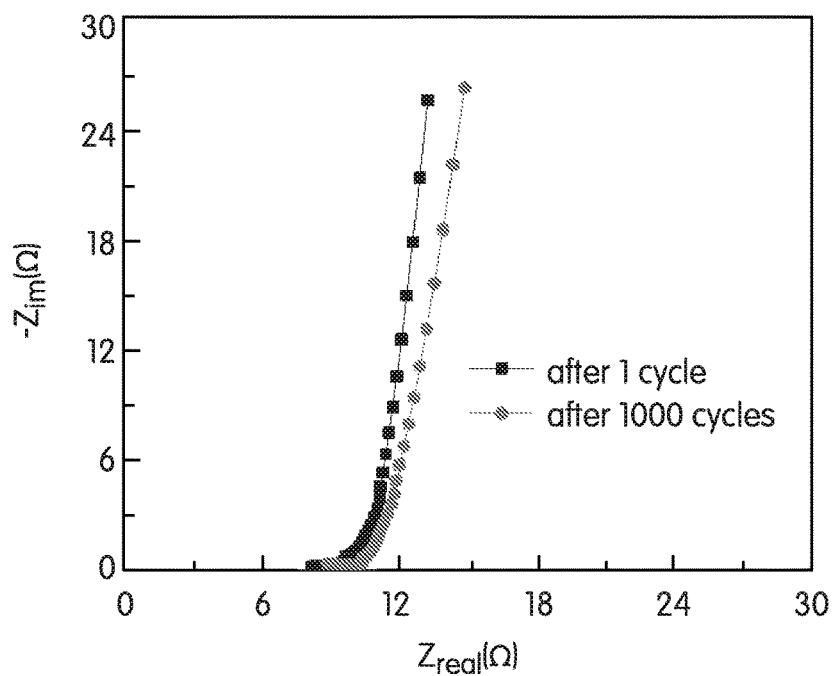
FIG. 10 is a graph of the electrochemical impedance spectroscopy (EIS) analysis for the supercapacitor of FIG. 2 before the first discharge cycle and after 1,000 charge-discharge cycles.
Figure 11:
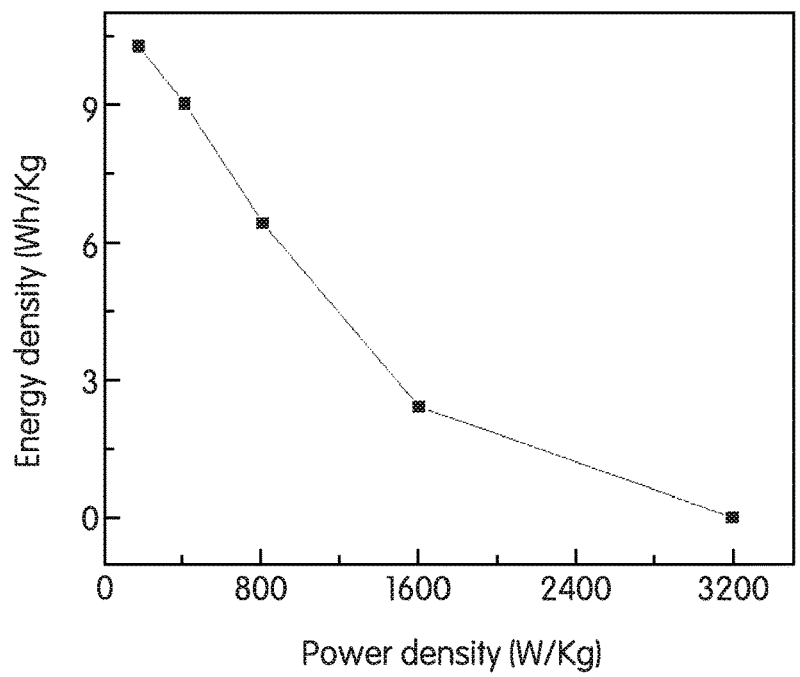
FIG. 11 is a graph of energy and power densities of the supercapacitor of FIG. 2 calculated from the constant current density charge-discharge curves measured with 250 mA/g, 500 mA/g, 1 A/g, 2 A/g, and 4 A/g.

FIG. 10 presents the electrochemical impedance spectroscopy (EIS) results after one cycle and 1,000 cycles using gelatin sheet with cheese as the packing materials. Only slight resistance increase was observed. FIG. 11 shows the energy and power densities curve calculated from the constant current density charge-discharge curves measured with 250 mA/g, 500 mA/g, 1 A/g, 2 A/g, and 4 A/g current densities.

The material possibilities of edible supercapacitors are immense due to the vast number of available food products. Other possible materials include monosodium glutamate (MSG, a flavor enhancer) as an electrolyte additive to increase the electrolyte ions density, carboxymethyl cellulose (CMC, a food additive) as a binder, silver leaf as a current collector, V8 vegetable drink and MONSTER ENERGY® drink as liquid electrolytes, BBQ sauce, JELL-O, and cheese as gel electrolytes, and gummy candy as a package material.

Figure 12:
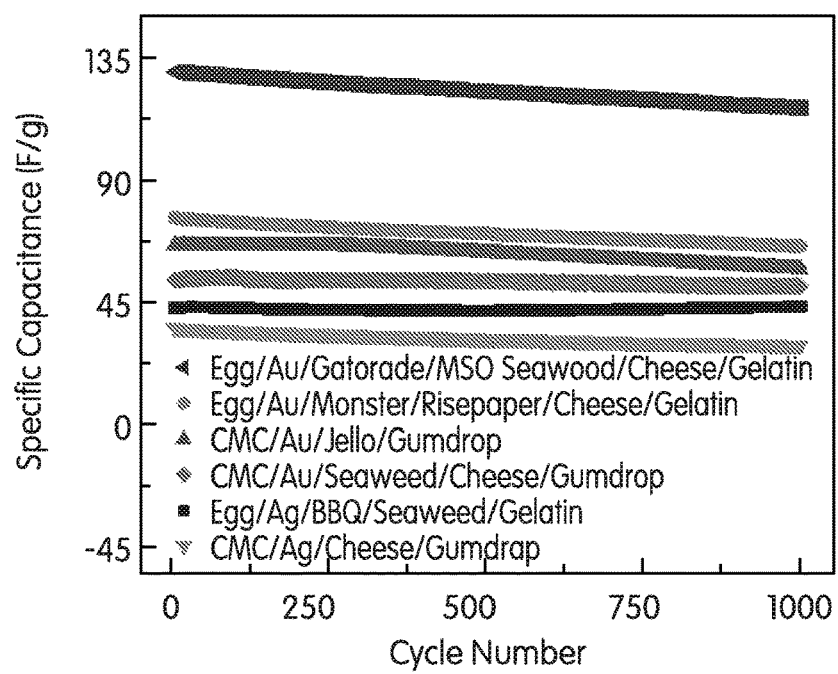
FIG. 12 is a graph of specific capacitance for six different supercapacitor material combinations for 1,000 charge-discharge cycles at a constant current density of 1 A/g.

FIG. 12 illustrates the specific capacitance over 1000 charge/discharge cycles for supercapacitors constructed of various different combinations of food-based materials. For 1,000 charge-discharge cycles at the current density of 1 A/g, the specific capacitance increases from 78.8 F/g to 129 F/g after the addition of MSG in GATORADE due to the increase of ion densities. The specific capacitances of other liquid electrolytes (V8 vegetable and MONSTER ENERGY drinks) show different values due to different ions components and concentrations. Due to high internal resistance, the specific capacitances with gel electrolytes (BBQ sauce, JELL-O, and cheese) are lower than those with liquid electrolytes.

Figure 13:
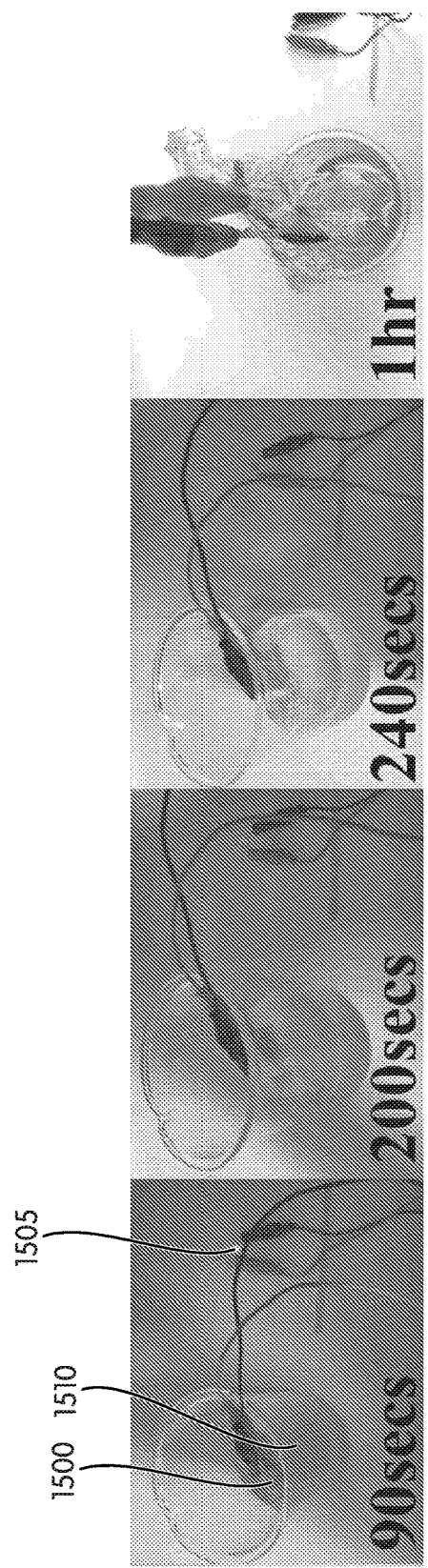
FIG. 13 is an elevation view of an experimental set-up with a series of three edible supercapacitors powering a light emitting diode (LED) while partially immersed in a simulated gastric fluid.

As discussed above, the edible nature of the food-based supercapacitors provides a swallowable power source for various types of medical devices. FIG. 13 illustrates three supercapacitors 1500 connected in series (each of the supercapacitor 200 having an electrode area of 2 cm by 2 cm) and powering a light-emitting diode (LED) 1505 while partially immersed in a simulated gastric fluid 1510. The LED 1505 remained lit for three minutes, followed by gradual diming and lack of emission after four minutes. After one hour, the supercapacitors 1500 were already partially dissolved in the simulated gastric fluid 1510.

Figure 14A:
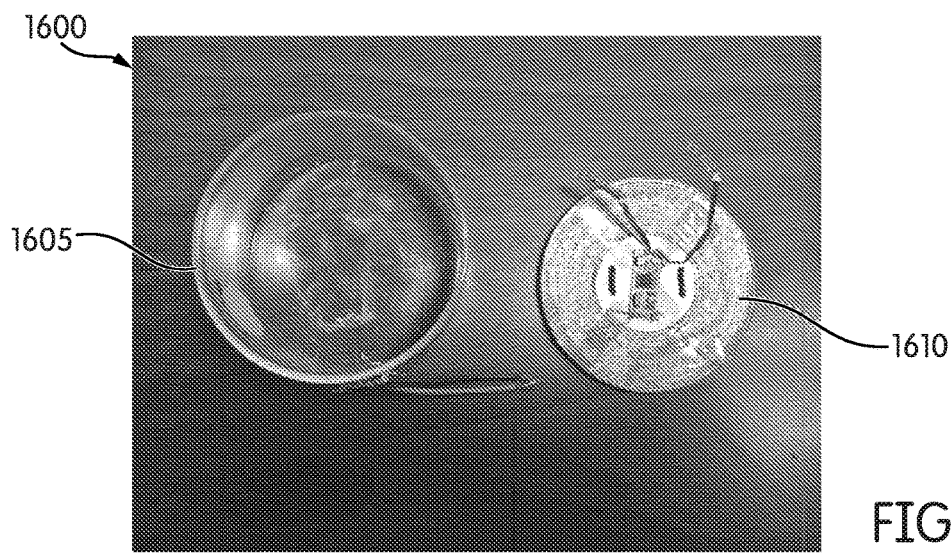
FIG. 14A is an overhead view of a wireless charging system for an edible supercapacitor including a transmitter chamber and a receiver lid.
Figure 14B:
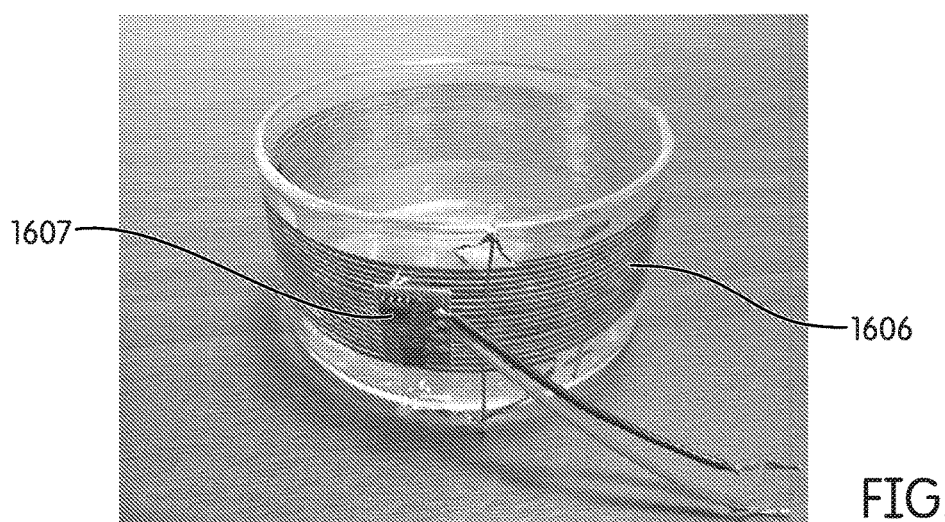
FIG. 14B is a perspective view of the transmitter chamber of FIG. 14A.
Figure 14C:
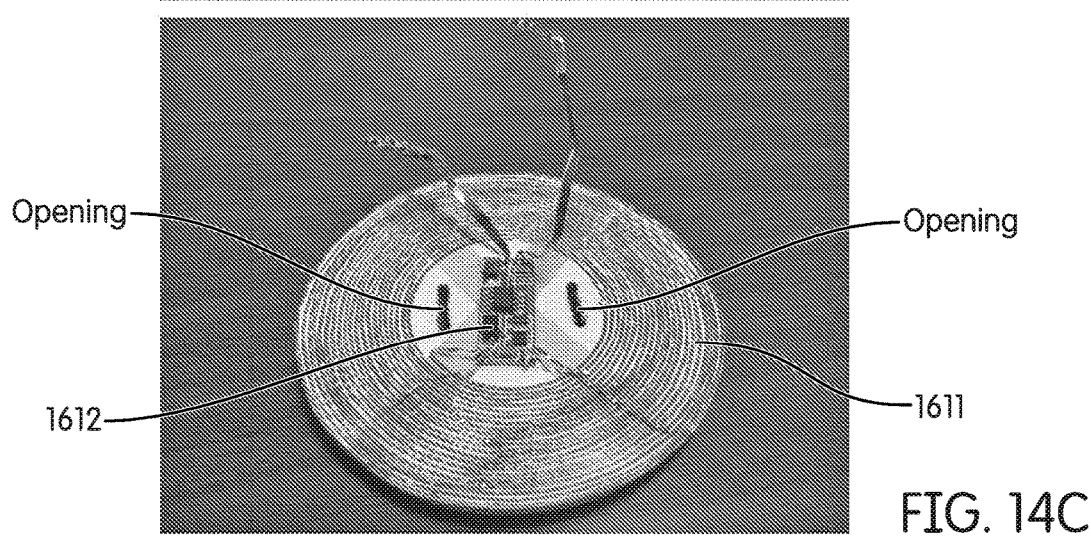
FIG. 14C is a perspective view of the receiver lid of FIG. 14B.
Figure 15:
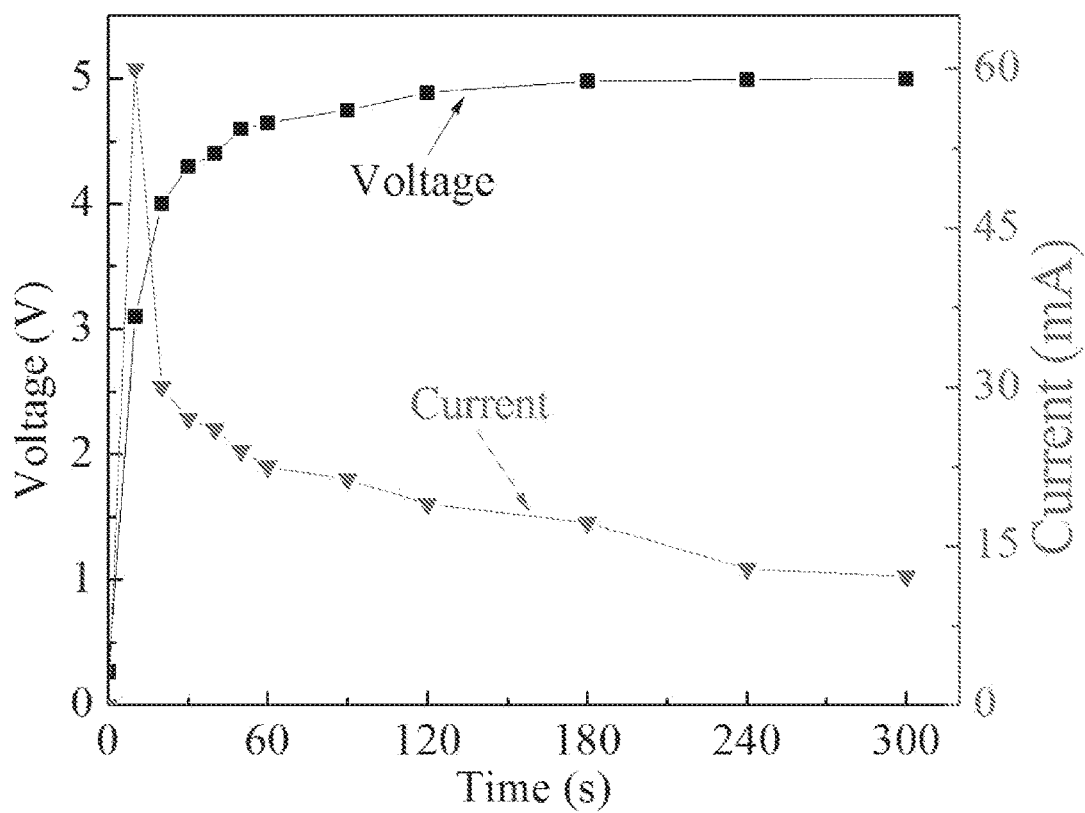
FIG. 15 is a graph of the current and voltage profiles during the wireless charging using the wireless charging system of FIGS. 14A-14C

FIG. 14A-14C illustrate another usage of the edible supercapacitor 200. In this example, a wireless charging system 1600 is provided to charge the supercapacitor 200 of FIG. 2. As shown in FIG. 14A, the wireless charging system 1600 includes a transmitter chamber 1605 and a receiver lid 1610. FIG. 14B is a close-up view of the transmitter chamber 1605 which includes a transmitter coil 1606 and a DC-AC converting circuit 1607 (GHH, Amazon). FIG. 14C is a close-up view of the receiver lid 1610 which includes a receiver coil 1611 and AC-DC converting circuit 1612 (GHH, Amazon). The supercapacitor 200 is integrated with the receiver coil 1611 and the AC-DC converting circuit 1612 and placed in a charging chamber that can then be charged wirelessly in an alternating electromagnetic field (with a frequency of 60 Hz) created by the transmitter coil 1606 and the DC-AC converting circuit 1607 outside the transmitter chamber 1605. Using a wireless charging system such as this, the supercapacitor 200 inside a human body can be charged in an alternating electromagnetic field that surrounds the human body. FIG. 15 illustrates a graph of the current and voltage profiles during the wireless charging using the wireless charging system of FIGS. 14A-14C. With 5.144 V constant voltage output from the receiver, the voltage of the supercapacitor set increases from 0.470 to 4.994 V, and the current decreases from 60 (measured at 10 s) to 14.41 mA in 3 minutes. After five minutes, the voltage increases to 5.002 V while the current drops to 12 mA Edible supercapacitors, such as illustrated in FIG. 2, can also be used to exploit the antibacterial activity of electric current. This antibacterial activity has previously been demonstrated against planktonic *Escherichia coli*, *Klebsiella pneumoniae*, and *Proteus* species in various liquids including synthetic urine, water, and salt solutions. Moreover, low-intensity electric current reduced the numbers of viable bacteria in staphylococcal and *Pseudomonas* biofilms after prolonged exposure (1 to 7 days). However, thus far, no real device has been implemented that can be taken into human body and used to kill bacteria via low-intensity electric current.

Figure 16:
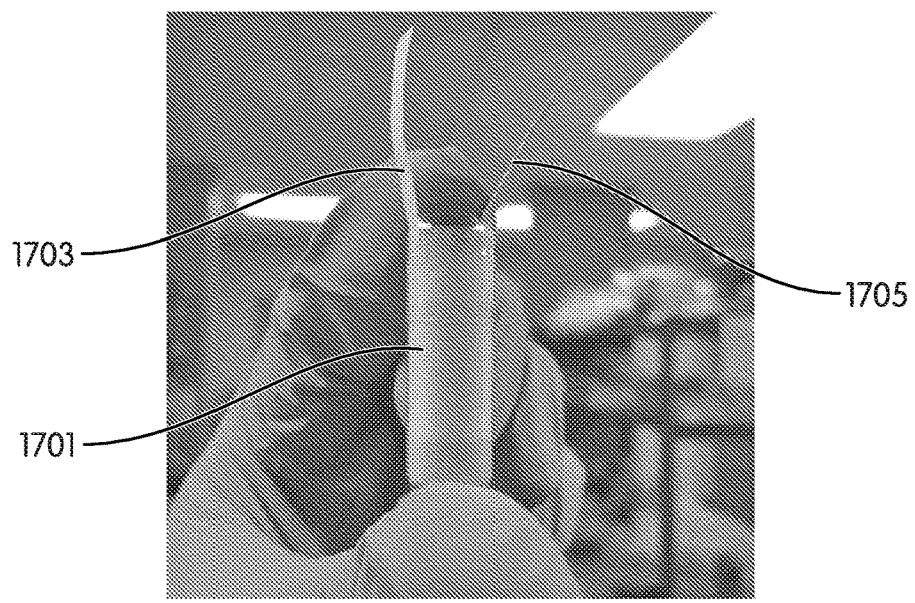
FIG. 16 is an elevation view of an edible supercapacitor packaged in a standard 000 size capsule.
Figure 17:
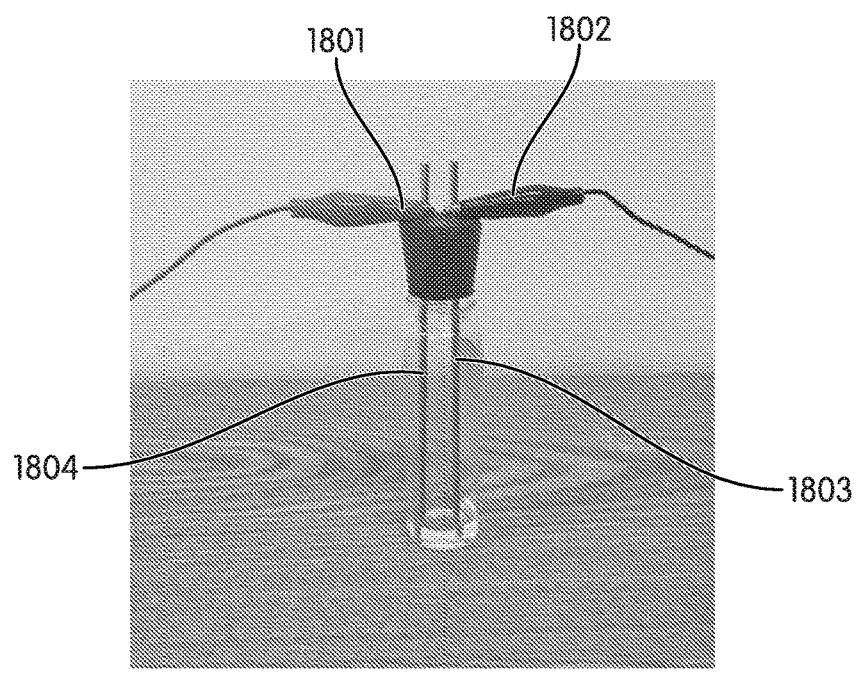
FIG. 17 is an elevation view of an experimental set-up for demonstrating the antimicrobial effect of the supercapacitor of FIG. 16 in a 3 mL *E. coli*-PBS suspension.
Figure 18:
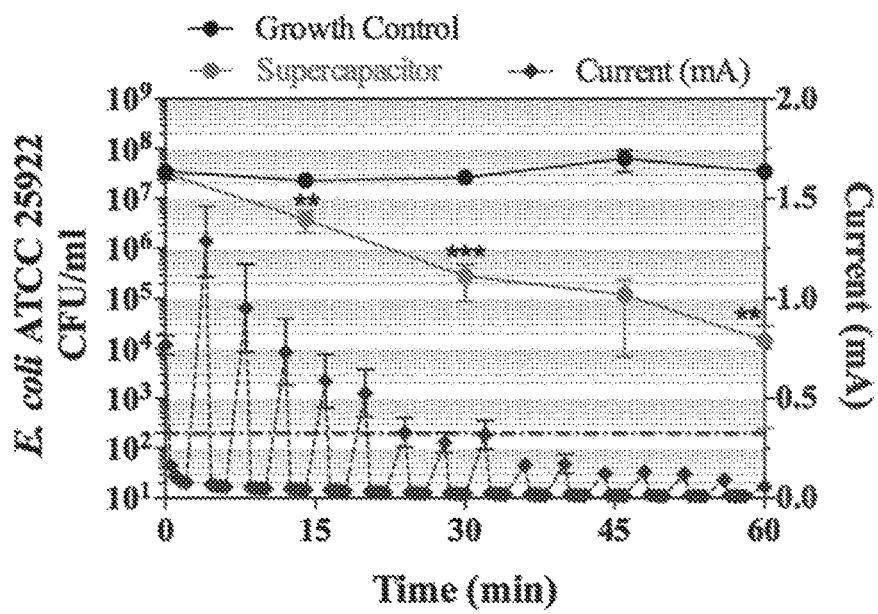
FIG. 18-21 are graphs of the mean colony-forming units (CFU) and standard error of the mean (SEM) for four different experiments where exponential-phase *E. coli* is exposed to alternating on-off supercapacitor mediated electrical current for 60-minutes using the experimental set-up of FIG. 17.
Figure 19:
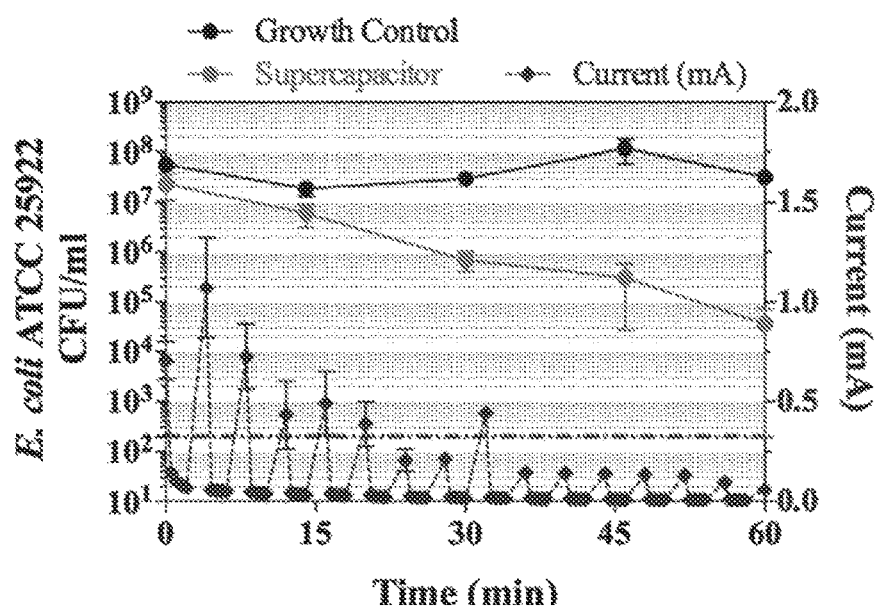
Figure 20:
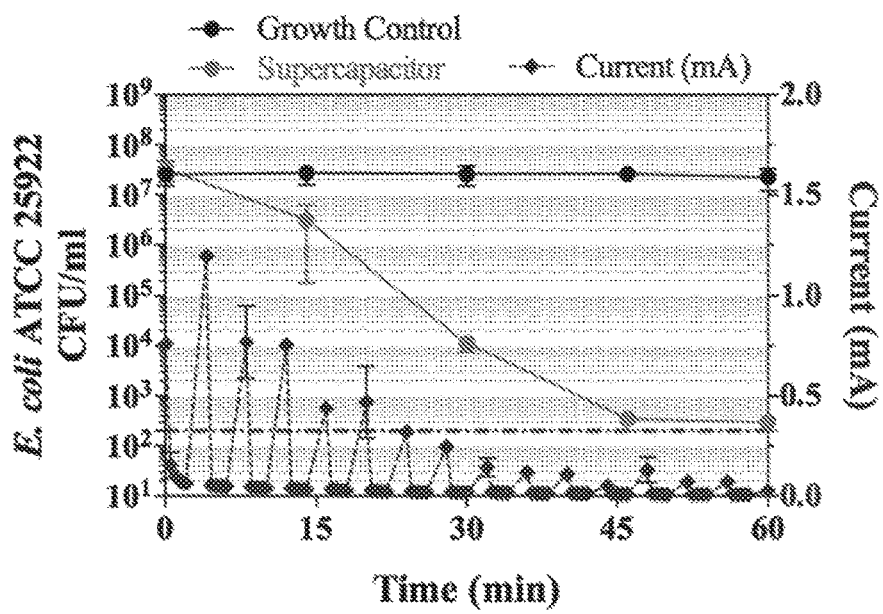
Figure 21:
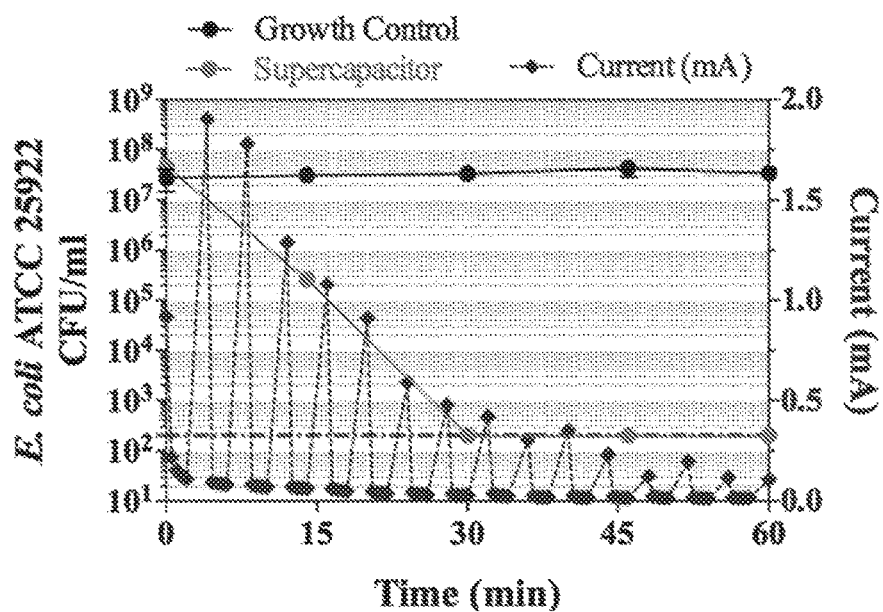

To further assess potential biomedical applications of the edible supercapacitor, the effect of edible supercapacitor-discharged electric current on bacterial viability was investigated using *E. coli* ATCC 25922 in broth antimicrobial susceptibility experiments. FIG. 16 shows the edible supercapacitor 200 packaged in a standard 000 size gelatin capsule 1701 with electrode contacts 1703, 1705 extending from the capsule 1701. FIG. 17 shows an experimental environment including two brass rods 1801 and 1802 with a stopper 1803 inserted into a 3 mL *E. coli*-PBS suspension 1804. The electric current loop was formed by connecting the outside ends of the rods to the electrode contacts 1703, 1705 of the supercapacitor 200. Exponential-phase *E. coli* cells (~$10^7$ CFU/mL) were re-suspended in phosphate-buffered saline (PBS) and exposed to alternating on (2 min) and off (2 min) cycles of electrical current for 60 min. Compared to no electrical current (growth control), a significant reduction ($P<0.01$) was detected in the number of viable cells present after exposure to supercapacitor-mediated electrical current for 60 min as illustrated in the graph of FIG. 18. A time-dependent reduction in bacterial viability was observed, with generally lower viable cell counts detected when electrical current was applied for longer periods of time. The edible supercapacitor 200 causes significant bactericidal activity reduction (99.93% average reduction) after 60 min of alternating on-off current exposures as illustrated in the graph of FIG. 18. When the replicate experiments were separated based on amperage readings, a higher amperage correlated with a greater reduction in bacterial viability at all time-points as illustrated in the graphics of FIGS. 18-21, suggesting that proper design of edible supercapacitors better controls the efficiency of antibacterial activity.

In addition to the specific methods and constructions described above, other mechanisms for manufacturing an edible supercapacitor are possible including, for example, using inkjet printing technology. As a direct-write technology, inkjet printing transfers a pattern directly onto a substrate providing fine/specific pattern generation, non-contact injection, solution saving effects, high repeatability and scalability, and processes easily applicable to large or small areas.

In one implementation utilizing inkjet printing technology, 0.2 g of active charcoal is added to 50 mL of distilled water. 0.04 g of CMC is then added as a binder. The active charcoal/CMC mixture is subjected to centrifugation (at 6000 rpm for 20 minutes) to remove large-sized particles and agglomerates, resulting in a suitable viscosity for the inkjet printing process. A silver (Ag) nanowire suspension is then prepared in water with sucrose ester as a dispersing agent. The silver nanowire suspension is then subjected to a sonication-driven scission process to avoid clogging of the inkjet printing hardware.

An inkjet-printed resistor can then be fabricated directly on paper (e.g., A4 paper) using a commercial desktop inkjet printer (e.g., an HP Deskjet F4810) with the active charcoal/CMC mixture as the "ink." To control the resistance of the resulting printed resistor, the same electrode pattern (e.g., a 2 cm wide rectangular shape) is printed/overwritten in the same position multiple times.

Figure 22:
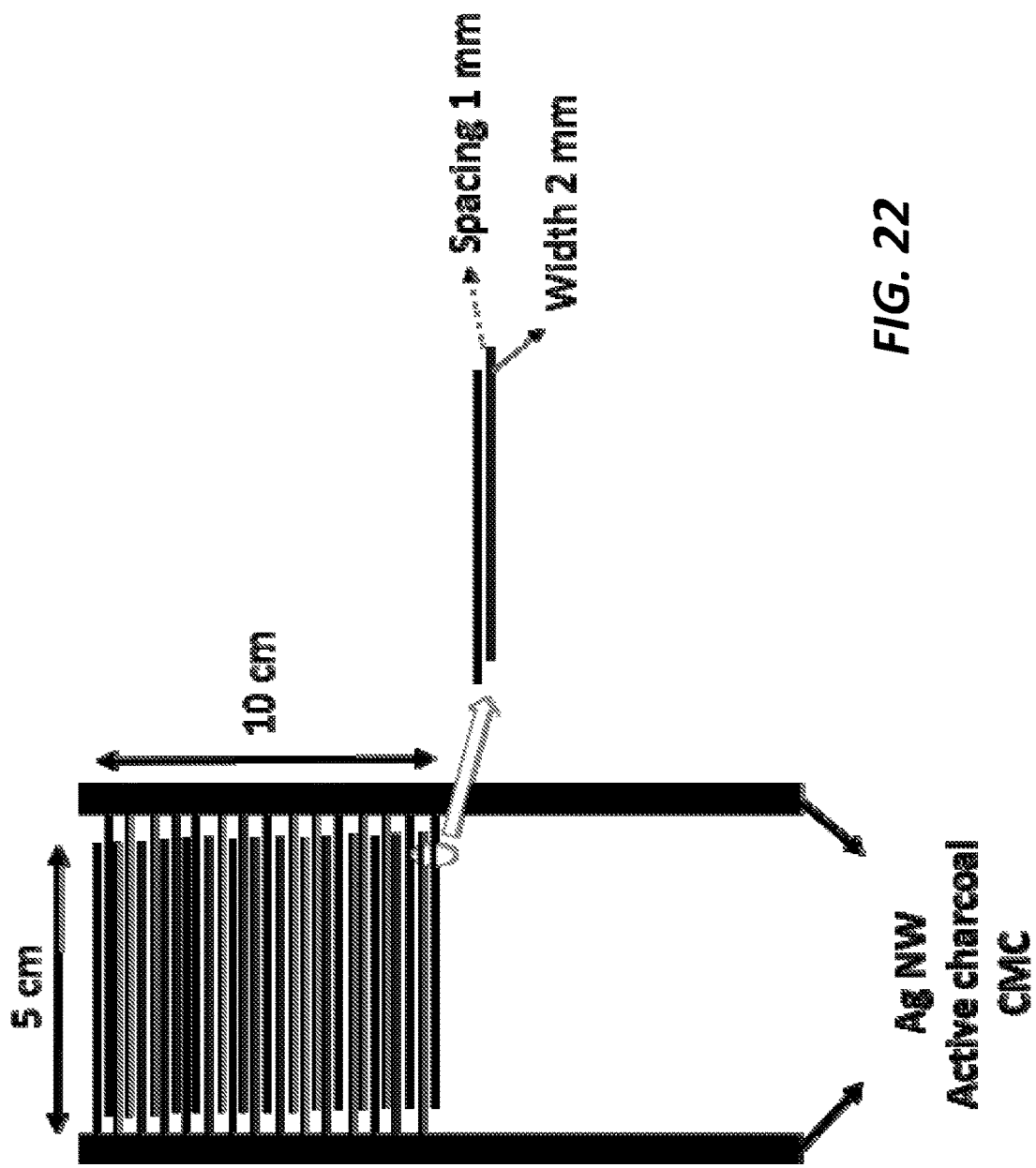
FIG. 22 is an overhead view of a patterned edible supercapacitor constructed using inkjet printing.

Similarly, to fabricate a supercapacitor electrode, the silver nanowire mixture is used as the "ink" to print a pattern on the paper. FIG. 22 illustrates one example of a patterned electrode printed by the inkjet printer to form the supercapacitor. This is followed by inkjet printing of the same pattern in the same position using the active charcoal/CMC mixture as the "ink." In order to form highly interwelded silver nanowire networks, the inkjet-printed supercapacitor electrodes are subjected to UV irradiation to allow for photonic sintering of the silver nanowires. The printed electrode is then coated with an electrolyte (such as, for example, GATORADE) and the inkjet-printed electrode/electrolyte assembly is then sealed with gelatin sheets as a supercapacitor package. The silver nanowire printed layer serves as a current collector, the active charcoal as the active material of the electrode, the CMC as the binder, the GATORADE as the electrolyte, and the gelatin sheets as the packaging.

The capacity of a supercapacitor manufactured using this "printing" technique can be adjusted and varied based on the number of times that the pattern is overwritten with the same "ink." In one implementation, where the mass load of the active charcoal is 0.2 mg and the actual capacity of the active charcoal is 100 F/g, the capacity of one electrode will be 0.02 F (i.e., 0.2 mg×100 F/g). Therefore, the whole capacity of the supercapacitor will be half of the electrode—that is 0.01 F. The capacity of the supercapacitor can be increased by increasing the number of times that electrode pattern is overwritten using the active charcoal/CMC mixture, thereby increasing the mass load of the active charcoal in the resulting printed electrode.

Thus, the invention provides, among other things, an edible supercapacitor that is truly edible and digestable as all components are originated from food products. The edible supercapacitors can be utilized in numerous biomedical applications including, for example, an electrical "antibacterial" for killing bacteria (e.g., E. coli) in vitro and a power source for a medical device such as, for example, a commercial USB camera. In addition to its antibacterial properties, the edible, food-based supercapacitors may be used as an oncological adjuvant for alimentary and other malignancies. By merging modern food engineering, materials science, device fabrications, and biomedical applications, this work has the potential to broadly and deeply impact the field of edible electronics as the horizon of search candidate materials for edible electronics has been unprecedentedly expanded. Various features and advantages of the invention are set forth in the following claims.

What is claimed is:

1. A capacitive power source comprising:
   an anode current collector;
   an anode electrode;
   a cathode electrode;
   a cathode current collector; and
   a separator positioned between the anode electrode and the cathode electrode,
   wherein the anode current collector, the anode electrode, the separator, the cathode electrode, and the cathode current collector are arranged in layers to form a symmetrical electric double-layer capacitor, and
   wherein the anode current collector, the anode electrode, the separator, the cathode electrode, and the cathode current collector are all formed of edible materials.

2. The capacitive power source of claim 1, further comprising a packaging material enclosing the anode current collector, the anode electrode, the separator, the cathode electrode, and the cathode current collector, wherein the packaging material is formed of an edible packaging material.

3. The capacitive power source of claim 2, wherein the packaging material includes at least one edible packaging material selected from a group consisting of gelatin, potato starch, soy lecithin paper, edible waxed paper, and edible waxed film.

4. The capacitive power source of claim 2, further comprising:
   a first conductive tab electrically coupled to the anode current collector and protruding from the packaging material; and
   a second conductive tab electrically coupled to the cathode current collector and protruding from the packaging material.

5. The capacitive power source of claim 2, further comprising a first segregation layer positioned between the packaging material and the anode current collector, the first segregation layer formed of at least one edible material.

6. The capacitive power source of claim 5, wherein the at least one edible material of the first segregation layer includes cheese.

7. The capacitive power source of claim 5, further comprising an edible electrolyte, wherein the first segregation layer is positioned to prevent the edible electrolyte from contacting the packaging material.

8. The capacitive power source of claim 1, wherein the edible material of the anode current collector includes a metal foil.

9. The capacitive power source of claim 8, wherein the metal foil includes gold or silver foil.

10. The capacitive power source of claim 1, wherein two or more layers selected from a group consisting of the anode current collector, the anode electrode, the separator, the cathode electrode, and the cathode current collector are coupled together using an edible, non-toxic binder.

11. The capacitive power source of claim 10, wherein the edible, non-toxic binder includes at least one selected from a group consisting of egg, egg powder, sugar, GellanGun, honey, extract juice from sticky food, and carboxymethyl cellulose.

12. The capacitive power source of claim 1, wherein the separator includes a porous insulator material.

13. The capacitive power source of claim 12, wherein the porous insulator material of the separator includes at least one selected from a group consisting of seaweed, air-dried meat, rice paper, pork casing, sugar sheet, vegetable paper, wafer paper, and tapioca paper.

14. The capacitive power source of claim 1, wherein the edible material of the anode electrode includes a porous conductive material.

15. The capacitive power source of claim 14, wherein the porous conductive material of the anode electrode includes at least one selected from a group consisting of activated charcoal, copper, magnesium, gold powder paste, and silver powder paste.

16. The capacitive power source of claim 1, wherein each material included in the capacitive power source is a food supplement, food additive, or an explicit food.

17. A method of operating the capacitive power source of claim 1, the method comprising:
coupling the capacitive power source to a medical device;
positioning the capacitive power source and the medical device in a digestive tract of a patient by swallowing;
powering the medical device with electrical power stored in the capacitive power source; and
allowing the capacitive power source to dissolve in the digestive tract by digestion.

18. The method of claim 17, further comprising reducing bacteria in the digestive tract by applying a current from the capacitive power source to a fluid medium within the digestive tract.

19. An edible supercapacitor comprising:
a first segregation layer formed of cheese;
a first current collector layer formed of edible gold leaf positioned adjacent to the first segregation layer;
a first electrode layer formed of activated charcoal positioned adjacent to the first current collector layer opposite the first segregation layer;
a separator layer formed of seaweed positioned adjacent to the first electrode layer opposite the first current collector layer;
a second electrode layer formed of activated charcoal positioned adjacent to the separator layer opposite the first electrode layer;
a second current collector layer formed of edible gold leaf positioned adjacent to the second electrode layer opposite the separator layer;
a second segregation layer formed of cheese positioned adjacent to the second current collector layer opposite the second electrode layer;
a packaging formed of gelatin enclosing the first segregation layer, the first current collector layer, the first electrode layer, the separator layer, the second electrode layer, the second current collector layer, and the second segregation layer; and
an edible electrolyte material enclosed within the packaging such that the first segregation layer and the second segregation layer prevent the edible electrolyte material from contacting the packaging.

* * * * *